United States Patent
Hingorani et al.

(10) Patent No.: US 10,588,866 B2
(45) Date of Patent: Mar. 17, 2020

(54) STABLE SOLID LIPID PARTICLE COMPOSITION FOR IMPROVED BIOAVAILABILITY OF LIPOPHILIC COMPOUNDS FOR AGE-RELATED DISEASES

(71) Applicant: VERDURE SCIENCES, Noblesville, IN (US)

(72) Inventors: Lal Hingorani, Noblesville, IN (US); Blake Ebersole, Carmel, IN (US)

(73) Assignee: Verdure Sciences, Noblesville, IN (US)

( * ) Notice: Subject to any disclaimer, the term of this patent is extended or adjusted under 35 U.S.C. 154(b) by 0 days.

(21) Appl. No.: 15/525,388

(22) PCT Filed: Nov. 11, 2015

(86) PCT No.: PCT/US2015/060143
§ 371 (c)(1),
(2) Date: May 9, 2017

(87) PCT Pub. No.: WO2016/077454
PCT Pub. Date: May 19, 2016

(65) Prior Publication Data
US 2017/0333362 A1 Nov. 23, 2017

Related U.S. Application Data

(60) Provisional application No. 62/078,271, filed on Nov. 11, 2014.

(51) Int. Cl.
| | |
|---|---|
| *A61K 9/16* | (2006.01) |
| *A61K 9/51* | (2006.01) |
| *A61K 31/12* | (2006.01) |
| *A61K 36/80* | (2006.01) |
| *A61K 9/14* | (2006.01) |
| *A61K 31/065* | (2006.01) |
| *A61K 9/50* | (2006.01) |
| *A61K 9/00* | (2006.01) |
| *A61K 31/047* | (2006.01) |

(52) U.S. Cl.
CPC .......... *A61K 9/5123* (2013.01); *A61K 9/0053* (2013.01); *A61K 9/0065* (2013.01); *A61K 9/145* (2013.01); *A61K 9/1617* (2013.01); *A61K 9/5015* (2013.01); *A61K 9/5115* (2013.01); *A61K 9/5192* (2013.01); *A61K 31/047* (2013.01); *A61K 31/065* (2013.01); *A61K 31/12* (2013.01); *A61K 36/80* (2013.01)

(58) Field of Classification Search
CPC ........ A61K 9/0087; A61K 9/009; A61K 9/14; A61K 9/141; A61K 9/143; A61K 9/145; A61K 9/16; A61K 9/1605; A61K 9/1652; A61K 9/1682; A61K 9/51; A61K 9/5107; A61K 9/5115; A61K 9/513; A61K 9/5161; A61K 9/5192
See application file for complete search history.

(56) References Cited

U.S. PATENT DOCUMENTS

| | | | |
|---|---|---|---|
| 5,861,415 A | 1/1999 | Majeed et al. | |
| 6,312,703 B1 | 11/2001 | Orthoefer | |
| 6,605,298 B1 | 8/2003 | Leigh et al. | |
| 8,273,375 B2 | 9/2012 | Lizio et al. | |
| 2007/0105912 A1* | 5/2007 | Holm | A61K 9/1611 514/355 |
| 2008/0166416 A1* | 7/2008 | Lizio | A61K 9/5026 424/494 |
| 2009/0324703 A1 | 12/2009 | Frautschy et al. | |
| 2010/0136105 A1 | 6/2010 | Chen et al. | |
| 2012/0178771 A1* | 7/2012 | Babul | A61K 9/1635 514/282 |
| 2013/0259937 A1 | 10/2013 | Howard et al. | |

FOREIGN PATENT DOCUMENTS

| | | |
|---|---|---|
| WO | 2007103435 A2 | 9/2007 |
| WO | 2013132457 A2 | 9/2013 |
| WO | 2014135967 A1 | 9/2014 |

OTHER PUBLICATIONS

Amirhossein Sahebkar, "Are Curcuminoids Effective C-Reactive Protein-Lowering Agents in Clinical Practice? Evidence from a Meta-Analysis", Phytotherapy Research, Phytother. Res. 28: 633-642 (2017), Published online Aug. 7, 2013 in Wiley Online Library (10 pages).
Written Opinion of the International Search Report, PCT/US2015/060143 dated Feb. 2, 2016 (5 pages).
International Search Report, PCT/US2015/060143 dated Feb. 2, 2016 (3 pages).
Extended European Search Report, EP 15 85 9032 dated Jul. 17, 2018 (8 pages).

* cited by examiner

Primary Examiner — Micah Paul Young
(74) Attorney, Agent, or Firm — Quarles & Brady LLP

(57) ABSTRACT

The present invention provides a delivery system which improves the stability, solubility and permeability of certain types of biologically active compounds in the gut after oral consumption. The delivery system comprises carrier granule comprising an agglomeration of solid lipid particles and a biologically active compound. The biologically active compound may be used with the delivery system to treat illnesses relating to inflammation, oxidation, or protein aggregation where a therapeutic blood and tissue level is required for treating the illness.

22 Claims, 13 Drawing Sheets

STABLE SOLID LIPID PARTICLE COMPOSITION FOR IMPROVED BIOAVAILABILITY OF LIPOPHILIC COMPOUNDS FOR AGE-RELATED DISEASES

CROSS-REFERENCE TO RELATED APPLICATIONS

This application represents the national stage entry of PCT International Application No. PCT/2015/060143 filed Nov. 11, 2015, which claims the benefit of U.S. Provisional Application No. 62/078,271 filed on Nov. 11, 2014, the contents of which are incorporated herein by reference for all purpose

FIELD OF THE INVENTION

The present invention generally relates to delivery systems for lipophilic compounds, particularly lipophilic compounds useful for age-related diseases.

BACKGROUND OF THE INVENTION

Pathogenesis of diseases like Alzheimer's and Parkinson's show mounting evidence of oxidative damage and inflammatory factors. Unfortunately, despite strong epidemiology and rationale, antioxidant and NSAID approaches to these age-related diseases have generally not been successful in the clinic. For example, vitamin E has failed in trials for Alzheimer's and heart disease prevention, while COX inhibitors have failed for Alzheimer treatment and been dropped for prevention efforts with traditional antioxidants (selenium, vitamin E, β-carotene), estrogens, and COX-2 inhibitors. The demographics of our aging population drive an urgent need for suitable alternatives for prevention and possible treatment of one or more of the chronic diseases of aging.

As a turmeric extract, curcumin is the yellow in yellow curries and is used as a food additive, for example, in yellow mustard. Like the "wonder drug" aspirin, which remains one of our few successful preventive agents, the long-term health potential of curcumin has a substantial history and a relatively well-established scientific basis. It has been identified as a major bioactive agent in an empirically developed system of traditional Indian and Chinese medicine.

Curcumin (diferulomethane) is not only a potent natural antioxidant and anti-inflammatory agent, acting on NFKB and AP-I regulated pro-inflammatory mediators including COX-2, iNOS, il-I and TNFα, but has multiple useful activities and has shown therapeutic potential in many pre-clinical culture and animal models for diseases, often related to aging. These include cancers (colon, prostate, breast, skin, leukemia, etc.) (Agarwal et al., 2003), prion disease (Caughey et al., 2003), atherosclerosis (Miguel et al., 2002; Ramaswami et al., 2004), stroke, CNS alcohol toxicity (Rajakrishnan et al., 1999), traumatic brain injury, Huntington's disease, Marie-Charcot Tooth, multiple sclerosis, and Alzheimer's disease.

Curcumin's structure, which includes both a lipohilic moiety and at least one hydroxyl group, resembles that of amyloid binding compounds. Amyloid dyes like Congo Red (CR) are known to bind via planar hydrophobic groups with appropriately spaced charge, and to suppress β-amyloid and other β-sheet-dependent peptide aggregation and toxicity. The Congo Red analogue, Chrysamine G, is more brain permeant and retains CR's amyloid binding properties. Curcumin shares the 19 angstrom CR spacing between its polar phenol groups; is readily brain permeant; and binds amyloid peptides, inhibiting their aggregation and toxicity in vitro. It has been discovered that curcumin effectively reduces amyloid accumulation in vivo in APP Tg mice. Because CR's anti-amyloid binding is generic and potentially relevant to other β-sheet intraneuronal aggregates including Huntington, a-synuclein, prions and tau, curcumin's anti-amyloid activity may be relevant beyond extracellular amyloid to intraneuronal aggregates. In fact, curcumin is one of the most effective anti-prion compounds ever tested in vitro, although it did not work in vivo with oral dosing of unstated formulation (Caughey et al., 2003). This raises the limitations of curcumin oral bioavailability.

The benefits of curcumin as a treatment for multiple diseases with aggregating amyloid proteins and other CAG repeat disorders are being established, and its efficacy in treating stroke, head trauma, metabolic syndrome, and many other conditions, including some forms of cancer and arthritis, as well as in promoting wound healing, is also beginning to be understood. All of these therapeutic applications are limited, however, because of poor intestinal absorption.

Although curcumin is an effective medication in multiple animal models for human diseases when given in chow at high doses (typically 2,000-5,000 ppm in diet in cancer trials), the current dogma is that it is so poorly bioavailable that it cannot be used for treatment outside the colon in humans. Curcumin is very hydrophobic and typically is not dissolved when delivered as a powder extract in common nutraceuticals. Most curcumin activities require 100-2,000 nanomolar (0.1-2 micromolar) levels in vitro, but current supplements result in negligible, low nanomolar blood levels (see Sharma et al., 2004). R. Sharma's group at Leicester has tried repeatedly and been unable to achieve significant blood levels beyond the low nanomolar range (Garcea G., Jones J. D., Singh R., Deunison A. R., Farmer P. B., Sharma R. A., Steward W. P., Gescher A. J., Berry D, P., "Detection of curcumin and its metabolites in hepatic tissue and portal blood of patients following oral administration," Br J Cancer, 2004 Mar. 8; 90 (5); 1011-5.) They and others conclude that delivery of effective concentrations of oral curcumin to systemic tissues (outside the GI tract) is "probably not feasible." Most of the literature supports this view, leading the NCI to focus on colon cancer.

Three factors limit curcumin absorption and need to be addressed: 1) rapid glucuronidation/sulfation of curcumin's phenolic hydroxyl groups and high "first pass" clearance; 2) curcumin is unstable in aqueous solution at pH 7 and above; and 3) curcumin is very hydrophobic and typically is not water soluble at acidic pH and when delivered as a dry powder in existing supplements. (Most of the curcumin is never absorbed and simply passes through the GI tract and is excreted.)

Solubilization is critical to prevent this, but curcumin requires pH 8.5 to dissolve completely. For this reason, cancer patients are taking huge doses, typically up to 8 gms a day. Diarrhea is a common side-effect. Garcea, G. et al. (2004) report that with patients taking 3.6 gms of curcumin a day (as a standard powder extract capsule supplied by Sabinsa Corporation), blood and liver levels achieved are negligible. They conclude that "[t]he results suggest that doses of curcumin required to furnish hepatic levels sufficient to exert pharmacological activity are probably not feasible in humans."

Curcumin is not soluble at acidic pH and breaks down when solubilized and diluted into water at neutral or alkaline pH (e.g., in the GI tract, after the small intestine), due to keto-enol transformations in the β-diketone bridge. In addition, curcumin is susceptible to rapid glucuronidation/sulfation. The major U.S. supplier, Sabinsa, has tried to make a more bioavailable form by adding Bioperine (piperine) to inhibit glucuronidation. Such an approach is flawed, however, because most glucuronidation takes place in the upper GI tract, where the pH is acidic, and curcumin is not completely dissolved until pH 8.5 and higher. Even worse, inhibiting glucuronidation can cause serious health risks. Glucuronidation is protective against many toxins and involved in the metabolism of commonly used drugs. Most elderly patients are on multiple drugs, at levels likely to be unsafely altered by inhibition of glucuronidation.

Curcuminoids are but one example of lipophilic compounds which have both a lipophilic moiety and at least one hydroxyl group. These compounds in general have problems of bioavailability as well as stability in an oral dosage form. Oral bioavailability requires stability, solubility and permeability of the active compound in the gut; however lipophilic compounds are generally not water soluble, and lipophilic compounds with hydroxyl groups may possess hydrolytic instability. Such solubility and instability issues are a substantial problem, both for bioavailability to the subject and for stability of the dosage form both in the gut and on the product shelf.

Dietary compounds and drugs which are water insoluble are found in a solid form in the gut. However, in order to absorb, a compound must either 1) dissolve in the water medium of the gut or 2) dissolve in the amphiphilic medium of the bile acid in the small intestine. A lipophilic compound containing one or more hydroxyl or acyl groups with a specific ratio of long-chain lipids allows for a greater level of colloidal dispersion.

Assuming a compound can achieve some level of solubility either in the aqueous or the lipid compartment of the gut, in both cases, the compound of interest is dispersed as an individual molecule in the medium, and exposed to oxidative (water) and hydrolytic (pH, enzymatic and microbial) conditions intended to break down and metabolize the compound, to excrete it from the body. In order to be absorbed intact, both the insolubility and instability issues must be addressed for a compound: addressing only one of these does not solve the problem.

Stability of a compound requires it to remain in a chemically electrostatically stable state in the medium in which it is found. ("Like dissolves like.") In the gut, water of both very low and very high pH predominates. Each extreme induces a charge on an active compound (particularly those containing an unstable hydroxyl group that can unfavorable for stability of the compound. Further, hydroxyl radicals are highly reactive and undergo chemical reactions readily. Compounds that are mostly nonpolar, but which contain a polar hydroxyl group are prone to degradation in varying pH due to the loss or gain of charge on the hydroxyl group.

Many compositions in the art improve bioavailability by a marginal sum, which is repeated in the art. Nanoparticles, micelles, liposomes have all been developed but few have made commercial success. One reason is due to their instability in the gut. Small particles possess a high amount of surface area exposed to the acid and alkaline pH and enzymes of the gut.

It would therefore be advantageous if a composition or delivery device which improves the stability, solubility and permeability of certain types of biologically active compounds in the gut after oral consumption, resulting in parent (native) compound levels that are therapeutic (as opposed to inactive metabolites such as glucuronides), could be formulated.

SUMMARY OF THE INVENTION

Figure 1:
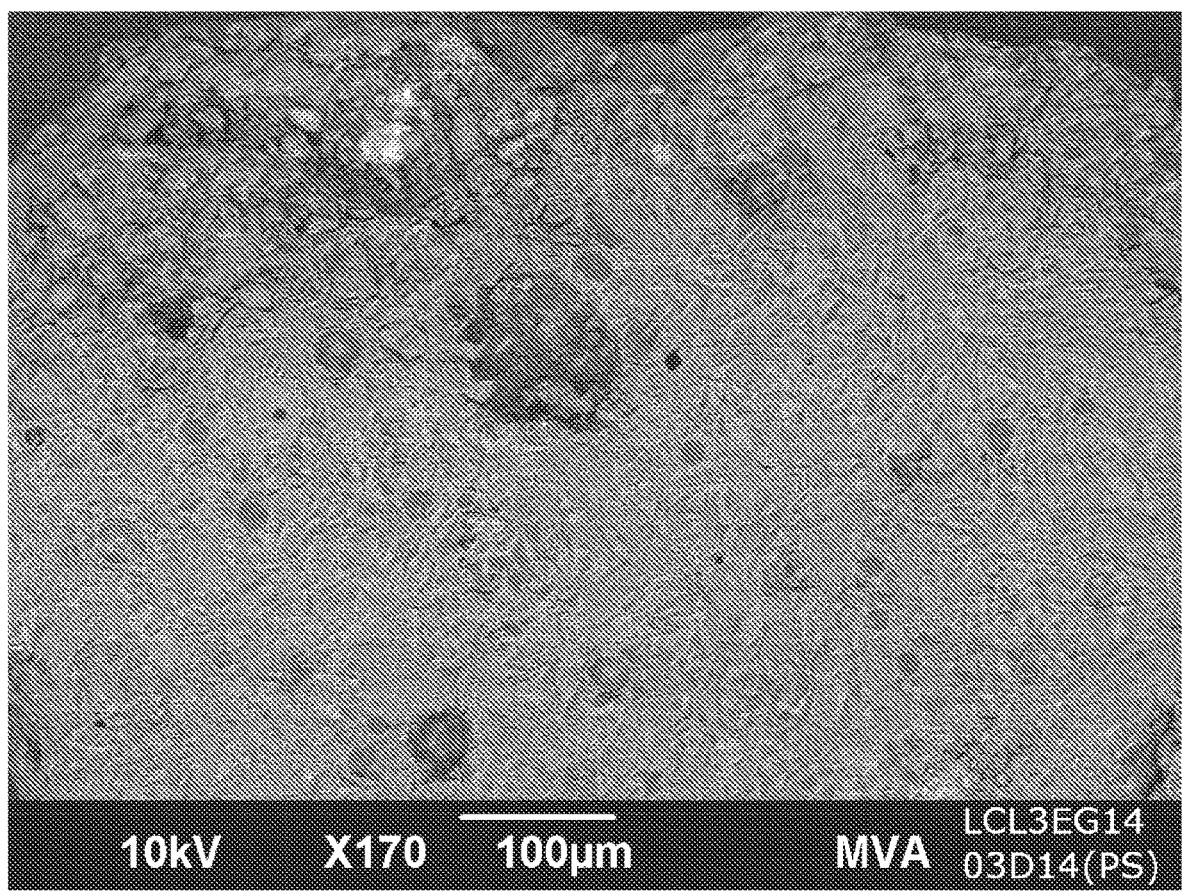
FIG. 1 is a scanning electron micrograph taken at 10 Kv and 170× magnification of a 30 mesh granule having a plurality of spherical solid lipid microparticles embedded in or adhered to the surface of the granule.

The present invention provides a delivery system which improves the stability, solubility and permeability of certain types of biologically active compounds in the gut after oral consumption, resulting in parent (native) compound levels that are therapeutic (as opposed to inactive metabolites such as glucuronides). The biologically active compound may be used with the delivery system to treat illnesses relating to inflammation, oxidation, or protein aggregation where a therapeutic blood and tissue level is required for treating the illness.

In an embodiment of the invention, the delivery system comprises an agglomeration of solid lipid particles for oral dosing, said particles comprising a specific ratio of long-chain lipids. The lipids possess a balance of positively and negatively charged groups ideal for stabilizing lipophilic compounds containing a hydroxyl group.

In one embodiment, the delivery system having enhanced oral bioavailability comprises a carrier granule, wherein the carrier granule comprises an agglomeration of solid lipid particles for oral dosing, and one or more biologically active compounds. In some embodiments, the carrier granule have a particle size from about 150 to about 840 microns. In some embodiments, the lipid spherical particles within the granule have a particle size from about 5 to about 20 microns.

In some embodiments, the present invention provides a method of treating a age-related disease comprising: administering an therapeutically effective amount of the delivery system as disclosed herein, wherein the delivery system comprises an active ingredient able to treat the age-related disease.

In further embodiments, the present invention provides a method of making a delivery system having enhanced oral bioavailability comprising the steps of: a) complexing an active ingredient with purified phosphatidylcholine (80-90% phophspatidylcholine) and ascorbyl palmitate; b) homogenizing the complex from step 1; c) filtering the homogenized complex; d) spray drying the homogenized complex; e) mixing the dried homogenized complex with melted stearic acid at high speed; and f) cooling and milling the material from step 4 to a powder of carrier granules.

DETAILED DESCRIPTION OF THE INVENTION

The present invention provides a delivery system, which is comprised of an agglomeration of solid lipid particles for oral dosing, said particles comprising a specific ratio of long-chain lipids. The lipids possess a balance of positively and negatively charged groups ideal for stabilizing lipophilic compounds containing a hydroxyl group. Such lipids useful for the particles include high-purity phosphatidylcholine (i.e. charged phospholipid), stearic acid (i.e. electrostatically balancing fatty acid), and ascorbyl palmitate (amphiphilic antioxidant), in a specific ratio or approximate range of ratio, as discussed further below.

The delivery system is used for the oral delivery of one or more active compounds. In one embodiment of the invention these active compounds are have a structure having both a lipophilic moiety and hydroxyl group possessing an overall non-water soluble nature, such as, but not limited to, carotenoids, fatty acids, polyphenols, lipophilic vitamins, flavonoids, isoflavones, curcuminoids, ceramides, proanthocyanidins, terpenoids, sterols, phytosterols, sterol esters, tocotrienol, squalene, and retinoids.

In one embodiment the active compound is a carotenoid, such as, for example, lutein, zeaxanthin, cryptoxanthin, or beta-carotene. In other embodiments the active compound may be one or more of omega fatty acids (e.g., DHA, EPA, CLA), polyphenols (e.g., ellagic acid, curcumin, proanthocyanidin), terpenoids (e.g., triterpenes, boswellic acid, phytosterols) lipophilic vitamins (e.g., Vitamin D, Vitamin E, Vitamin K), flavonoids, stilbenes (resveratrol) isoflavones, phytosterols, or sterol esters. The term "biologically active compound" or "active compound" or "active ingredient" are used interchangeably herein. The active compound may include a botanical extract (that may have one or more active compounds), curcuminoids, lutien, ubiquinone (CoQ10), Boswellic acids, Bacopa glycosides, Withanolides, thymoquinone, triterpene glycosides, and the like. Suitable active compounds are compounds that contain both a lipophilic moiety and hydroxyl group. This list is not intended to be exhaustive, and one of skill in the art would readily appreciate other such lipophilic compounds that could also be used with the inventive delivery compound/system.

In one embodiment, an oral dosage formulation may comprise an active ingredient, phosphatidylcholine, stearic acid, and ascorbyl palmitate. Dextrin and silicon dioxide may also be used. In accordance with a further embodiment, the oral dosage may include the individual components in relative parts as follows:

Active: 10-30%
Phosphatidylcholine: 10-20%
Stearic acid: 25-35%
Dextrin: 25-40%
Ascorbyl palmitate: 1-4%
Silicon dioxide: 0.1-3%

Suitably, the oral dosage formulation is prepared using a ratio of stearic acid to phosphatidylcholine (PC) that exceeds 1. In certain embodiments, the ratio of stearic acid:PC is in a range of about 1.25:1 to about 3.5:1.

In another embodiment, the delivery system may include:
Active compound—15-40%
Soya lecithin—7-25%
Maltodextrin: 7-30%
Ascorbyl palmitate: 1-3%
Silicone dioxide 0.3-2%

In some embodiments, the soya lecithin is phosphatidylcholine.

The oral delivery system is suitably in the form of an agglomeration or plurality of solid lipid microparticles containing an active ingredient embedded in or adhered to the surface of carrier granule. For example, as shown in FIG. 1, a plurality of spherical solid lipid microparticles having a core of an active ingredient, including curcumin and/or lutein, phosphatidylcholine, and ascorbyl palmitate and coating of stearic acid are embedded in or adhered to the surface of granule which acts as a carrier for the microparticles. In accordance with certain embodiments, the granules have particle size in the range of about 20 to about 90 mesh (i.e., between about 150 microns and about 840 microns). The spherical solid lipid particles have a particle size in the range of about 5 to about 20 microns. In accordance with certain other embodiments, the granules may further include solid lipid microparticles fully encased within the granule matrix. The carrier granule is generally formed from fractured solid lipid microparticles produced during the manufacturing process.

Without being bound thereby, it is believed that by providing an agglomeration or plurality of solid lipid microparticles embedded in or adhered to a carrier granule, the delivery system acts to protect the hydroxyl group of the active ingredient from hydrolysis in the gut thus improving the stability of the active ingredient. It is also believed that the oral delivery system encourages direct lymphatic absorption of the lipophilic active ingredient through the chylomicron thereby avoiding first pass metabolism in the liver (i.e., glucuronidation) and increasing bioavailability of the active ingredient.

The properties of the invention are an oral delivery system which improves the stability, solubility and permeability of certain types of biologically active compounds in the gut after oral consumption, resulting in parent (native) compound levels that are therapeutic (as opposed to inactive metabolites such as glucuronides). The biologically active compound may be used to treat illnesses relating to inflammation, oxidation, or protein aggregation where a therapeutic blood and tissue level is required for treating the illness.

The oral delivery system may be used with certain types of biologically active compounds for treatment of a number of age-related diseases, for example, but not limited to, age-related diseases, neurodegenerative diseases, Alzheimer's disease, Parkinson's disease, macular degeneration, dementia, osteoarthritis, and the like.

The inventive oral dosage formulation has demonstrated increased solubility and stability.

Solubility data on curcumin solid lipid microparticles embedded on or adhered to the surface of a carrier granule (SLCP)**:

TABLE 1

| Test formulation | Solubility in water % | Solubility in water (µg/mL) | Fold improvement |
|---|---|---|---|
| Curcumin (unformulated)* | 0.00006 | 0.6 | 1 |
| SLCP-1 | 14 | 140,000 | 233000 |
| SLCP-2 | 76 | 760,000 | 1270000 |

*Biji T. Kurien, Anil Singh, Hiroyuki Matsumoto, and R. Hal Scofield, Improving the Solubility and Pharmacological Efficacy of Curcumin by Heat Treatment ASSAY and Drug Development Technologies. August 2007, Vol. 5, No. 4: 567-576 source: http://online.liebertpub.com/doi/abs/10.1089/adt.2007.064
**5% w/v in DI water at 37° C.
Note:
SLCP1 is ~30 mesh (about 595 microns) while SLCP2 is ~80 mesh (about 175 microns) powder (Mesh = number of squares per linear inch).

In one embodiment, the oral delivery system including an active compound may be made using the following steps:
(1) Complexing the active ingredient in solution with purified PC (80-90% phosphatidylcholine—expensive and typically used only for injectable drugs) and ascorbyl palmitate;
(2) Homogenizing the complex from Step (1) at high speed with additional ascorbyl palmitate, dextrin, and, optionally, silicon dioxide at high speed;
(3) Filtering and spray drying the homogenized complex;
(4) Mixing the spray-dried powdered complex with heated (melted) stearic acid at high speed; and
(5) Cooling and then milling the material from Step (4) to a powder including granules having agglomerated and/or a plurality of solid lipid microparticles embedded in or adhered to the surface of the granules.

Any solvent suitable for dissolving the active ingredient(s), the phosphatidyl choline, and the ascorbyl palmitate may be used in Step (1). In accordance with embodiment, the solvent used in Step (1) may include ethyl acetate.

The oral delivery system disclosed herein addresses several issues associates with the oral therapeutic use of active ingredients having both a lipophilic moiety and at least one hydroxyl group.

PROBLEM: One of the major challenges with dissolved compound is their permeability through cell membranes. This may be due to inadequate charge on the active compound. The present invention solves such problem.

PROOF: Presence of phosphatidylcholine, stearic acid, ascorbyl palmitate, all long-chain lipids.

Figure 2:
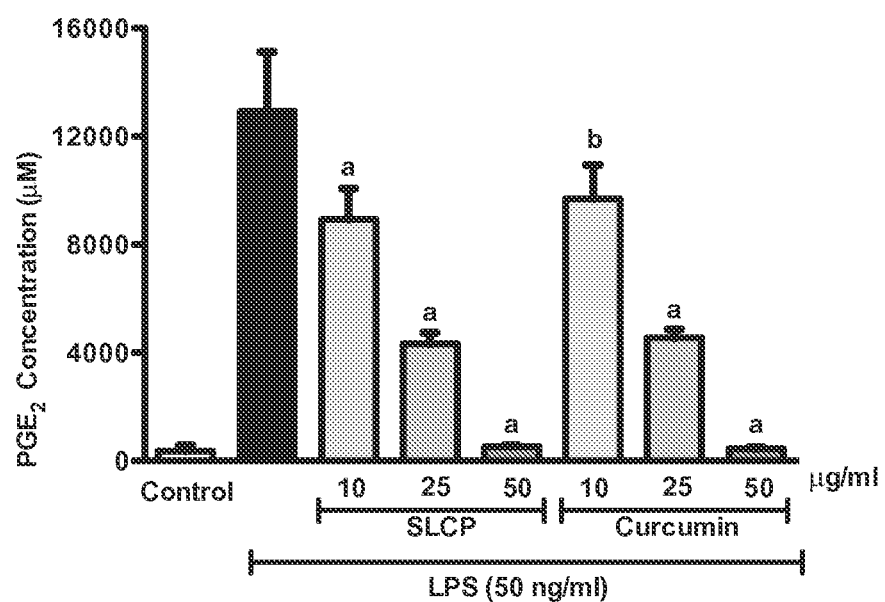
FIG. 2 is a graph demonstrating solid lipid microparticles (SLCP) dose-dependent inhibition of prostaglandin production.

Solid lipid microparticles (SLCP) are permeable into cultured cells where they dose-dependently inhibit prostaglandin production after stimulation with lipopolysaccharide (LPS) as shown in FIG. 2. (Data obtained October 2013, unpublished).

Example 1: Curcumin

PROBLEM: Compounds that do achieve solubility, stability and permeability are rapidly metabolized by the liver into inactive conjugated metabolites. Curcumin is insoluble in water at neutral and acidic pH, and it rapidly hydrolyzes, or breaks down in alkaline conditions of the small intestine. Once consumed, curcumin fail to fulfill the three major requirements for bioavailability: solubility, permeability, and stability. Approached to address this issue have not resulted in studies finding detectable levels of curcumin. Products that mix curcumin in oils, process it into micronized or nanoparticles, or add piperine have all failed to result in blood levels of curcumin.

The present invention allows for increased uptake of active compound onto the chylomicron and into the lymphatic system, allowing immediate exposure to cells. When curcumin is combined with these in a specific way, it becomes dissolvable in the small intestine, protected from the alkaline and adsorbed onto the chylomicron Data showing preferential uptake of curcumin into lymph fluid with this formulation, after single oral dosing by rodents, shown below (Data obtained May 2014, unpublished).

Following previously published designs, a total of ten Sprague-Dawley rats received a single oral administration of 75 mg curcumin/kg body weight as either a standard aqueous suspension (Curcumin from Sigma # C7727) or solid lipid curcumin microparticles (SLCP) prepared as described above. Prior to treatment, the rats were anaesthetized followed by a surgical intervention to cannulate the mesenteric mesenteric lymph duct (for lymph collection) and the carotid artery (for blood collection). The cannulas were externalized and the rats were allowed to recover for 24 hours. Thereafter, either the curcumin suspension or the SLCP dosage form was administered via gavage. Blood (0.25 ml) was sampled prior to and 0.5, 1.0, 2.0, 3.0 and 5.0 hours after administration into vials coated with EDTA. Blood samples were centrifuged to obtain plasma and stored at <−30° C. until analysis. Mesenteric lymph (0.25 ml) was collected prior to and 1 and 5 hours after administration into vials coated with EDTA and stored at <−30° C. until analysis.

Analysis of curcumin and glucuronated curcumin was performed by HPLC with UV-detection coupled to MS according to published methods. The analytical method was validated including stability of curcumin and curcumin glucuronide in blood/plasma and lymphatic fluid. The Limit of Determination was set to 2.5 ng/ml biological fluid.

Results and Discussion

Figure 3:
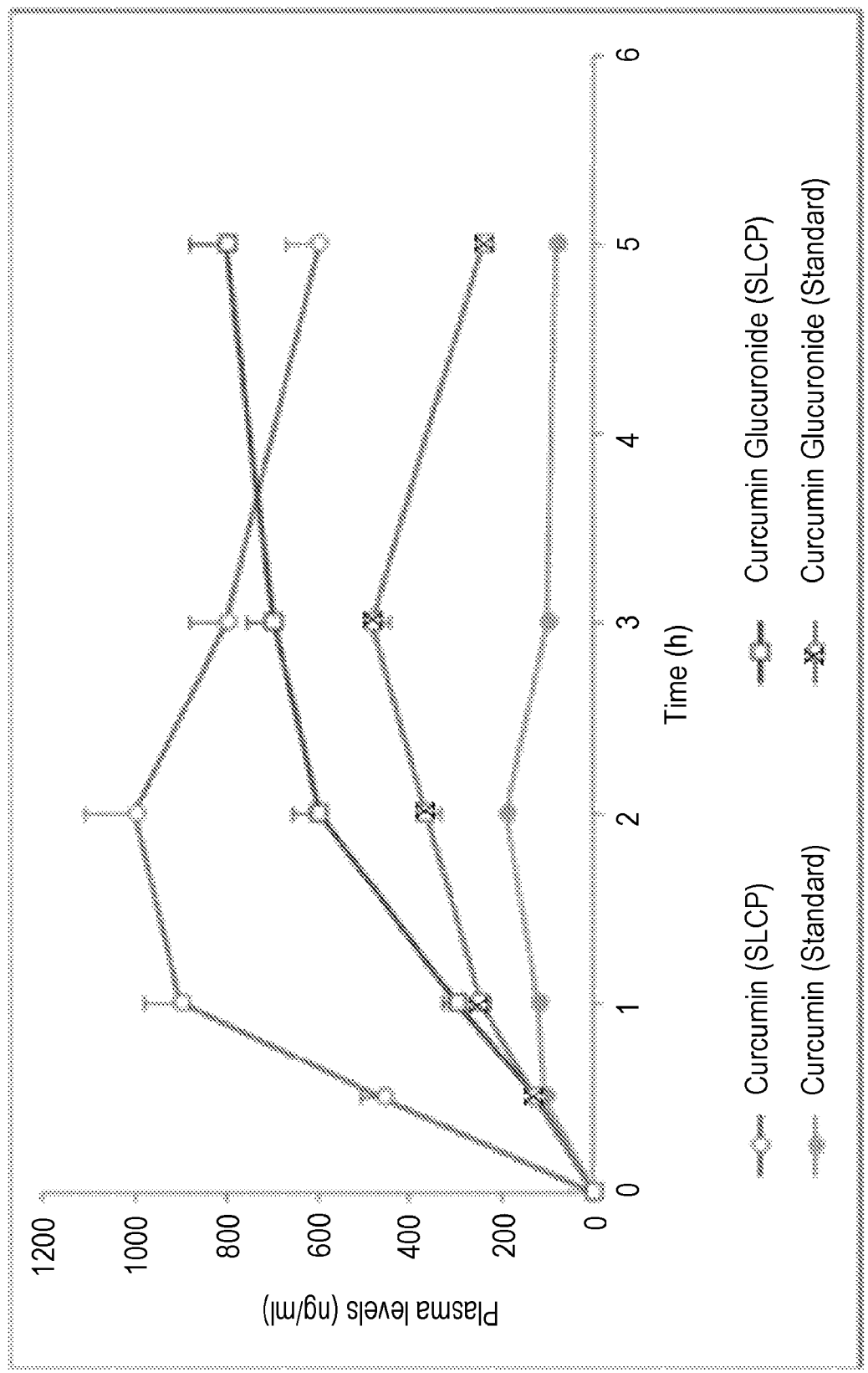
FIG. 3 is a graph demonstrating plasma concentrations of free and glucuronated curcumin (mean values±s.d.; n=5).

As seen on FIG. 3 and Table 2, the plasma concentration of curcumin is substantially higher after administration of SLCP dosage form when compared to the standard curcumin suspension. In addition, the ratio of free to glucuronated curcumin indicates that after administration of SLCP dosage form a substantial higher fraction of free curcumin reaches the blood stream when compared to the standard curcumin suspension. The pharmacokinetic test results suggest a 5-times higher relative bioavailability of curcumin after administration of SLCP dosage form when compared to the standard curcumin suspension.

TABLE 2

|  | Curcumin | | Curcumin Glucuronide | |
| --- | --- | --- | --- | --- |
| Parameter[†] | SLCP | Standard | SLCP | Standard |
| $C_{max}$ (ng/ml) | 1000 | 190 | 800 | 483 |
| $AUC_{0-t}$ (ng × ml/h) | 3704 | 562 | 2736 | 1579 |

Figure 4:
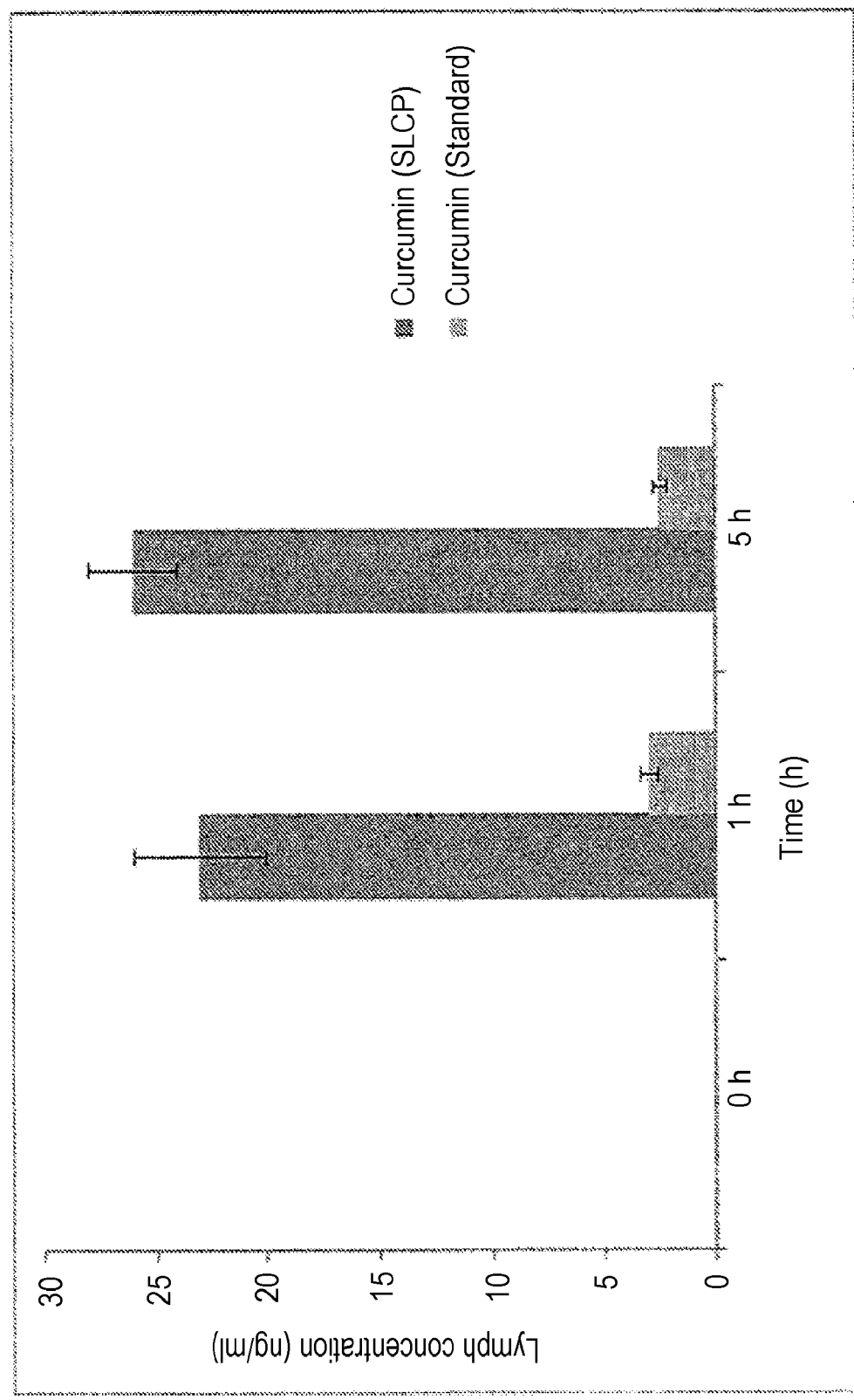
FIG. 4 is a graph showing lymphatic fluid concentrations of curcumin (mean values±s.d; n=5).

[†]$C_{max}$: Maximum concentration observed;
$AUC_{0-t}$: Area Under the plasma concentration/time Curve from time 0 to the last plasma concentration determined In FIG. 4 the lymphatic concentrations of curcumin are shown. About 10-fold higher concentrations of curcumin were observed after administration of SLCP when compared to the standard curcumin suspension.

The high amount of curcumin found in the lymphatic fluid after treatment with SLCP serves as explanation for its increased bioavailability when compared to the standard curcumin suspension.

It is well known that curcumin undergoes extensive first-pass metabolism yielding high amounts of curcumin-glucuronide in the blood after oral administration. The lymphatic transport of curcumin after oral administration circumvents the liver and the first-pass metabolism. An increased curcumin transport through the lymphatic system prompts the delivery of higher amounts of curcumin into the blood stream.

Example 2: Lutein

PROBLEM: Lutein (lipophilic compound with hydroxyl group) is insoluble in water, and the portion of lutein which is soluble rapidly degrades upon exposure to water.

SOLUTION: The technology disclosed herein stabilizes actives in this class.

Human Lutein Bioavailability data (obtained August 2014, unpublished) demonstrates an increase in the bioavailability of lutein formulated as in the oral delivery system discloses above (Lutein SLP) versus conventional lutein as shown in Table 3.

TABLE 3

|  | Conventional Lutein (ng/mL) | Lutein SLP (ng/mL) |
| --- | --- | --- |
| Pre | 59 ± 6 | 52 ± 7 |
| Post | 111 ± 14 | 345 ± 49 |
| Change | 52 ± 13 | 293 ± 50 | p = 0.001 by unpaired t-test

PROBLEM: the art on lutein bioavailability is not clear as to whether free or esterified lutein is better absorbed—both appear to be equally absorbed.

SOLUTION: This invention clarifies the art and uses lutein ester (form found in nature) as the active component in order to achieve stable levels in the bloodstream as shown in Table 3, above.

PROBLEM: Lutein esters are typically found in nature as diesterified forms, with two fatty acid groups occupying the sites of the hydroxyl groups normally found in lutein, e.g., as lutein dipalmitate. However, most free lutein on the market requires a very high concentration which is not cost-effective, and is extracted with harsh/toxic solvents.

SOLUTION: This technology allows for the use of the natural form (ester) without chemical reactions to de-esterify or toxic solvents Additional problems or issues encountered when formulating oral dosage forms of lipophilic compounds having at least one hydroxyl group addressed by the disclosed oral delivery system include: the use of components not suitable for food use to address bioavailability and/or stability issues and the use of delivery systems that are not stable in gut.

PROBLEM: Solid Lipid Nanoparticles (SLN), liposomes etc. targeting lymphatic transport are often unstable in the gut. Improvements in oral bioavailability of nanoparticles as a result are often limited.

SOLUTION: Solid Lipid Particles that are an agglomeration of microparticles are stabilized in the varying pH and aqueous environment of the gut, allowing for lymphatic transport. The composition is a powder made of an agglomeration of coated microparticles, with powder size being between 20 and 90 mesh, and with particle size in the agglomeration being in the range of 5-20 microns. The agglomeration of particles allows for less surface area exposed to the stomach acid and bile.

PROBLEM: Most products on the market either have failed in clinical efficacy trials, do not reach therapeutic blood levels, or require doses higher than practical in order to work SOLUTION: Clinical data on low doses of curcumin and boswellic acid SLP is available showing efficacy.

The oral delivery system and therapeutic compositions of the present invention may be formulated into any suitable oral nutraceutical or pharmaceutical dosage forms including, but not limited to, tablets, capsules, powders, liquids, chews, gummies, etc. using standard excipients and formulation techniques in the industry.

Example 3: Plasma Lutein Concentrations in Adult Subjects

This example demonstrates the increased bioavailabilty of lutein when paired with granules of the present technology when compared to conventional lutein.

Method

Study protocol was approved by the Ohio Health Institutional Review Board. All subjects signed an informed consent form. Subjects were 12 males and females (six of each gender) aged 52 to 69, mean±SD of 57±3 for the standard lutein, and 59±6 for the novel lutein complex. Based on answers to an eligibility questionnaire, the accepted subjects were nonsmokers who were free from problems that cause widespread oxidant stress or cause problems with absorption of lipid nutrients. Also, based on answers to the questionnaire, subjects did not consume eggs, spinach, or kale more than four times a month, nor take lutein supplements.

Subjects were randomly assigned to either lutein ester or a solid-lipid particle (SLP™) complex lutein. The latter was supplied by Verdure Sciences, Noblesville, Ind., USA. The subjects took a single capsule of 10 mg lutein for 10 days (same mg of lutein/day/treatment, though different weights of total powder). Subjects were blinded to group assignment. The capsules were taken with a self-selected meal containing at least 200 Calories of fat. The subjects provided a blood sample in a heparin containing tube before and after the 10-day supplementation period as well as 7 days after discontinuing the supplement. Plasma was separated by centrifugation for 30 min at 3000 rpm. Plasma lutein was determined by HPLC.

Figure 5:
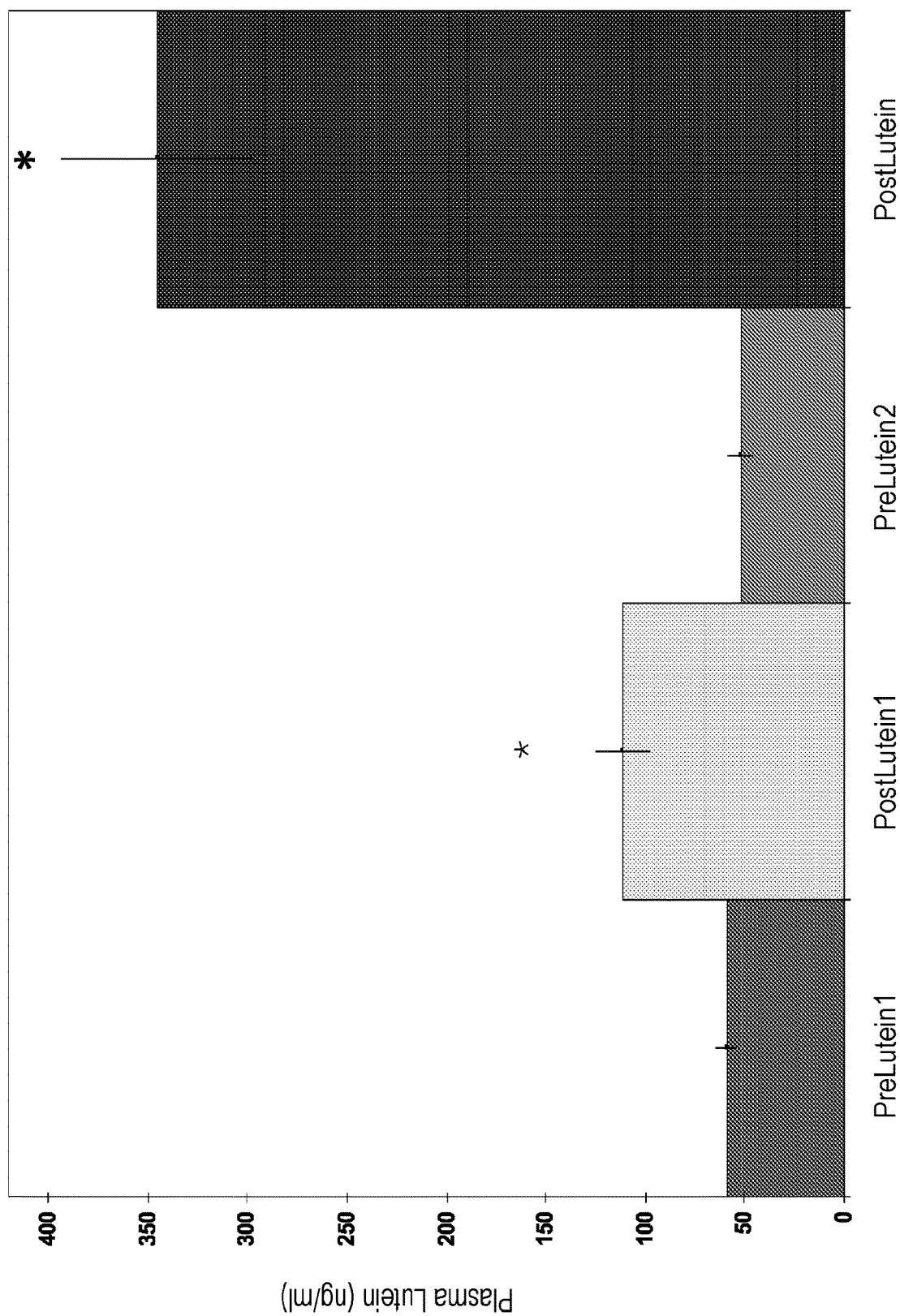
FIG. 5 is a graph showing plasma lutein concentrations before and after 10 days supplementation with 10 mg/day of lutein. Lutein 1=lutein ester. Lutein 2=solid-lipid particle complex lutein. *Significantly different from pre value, $p<0.001$, paired t-test.
Figure 6:
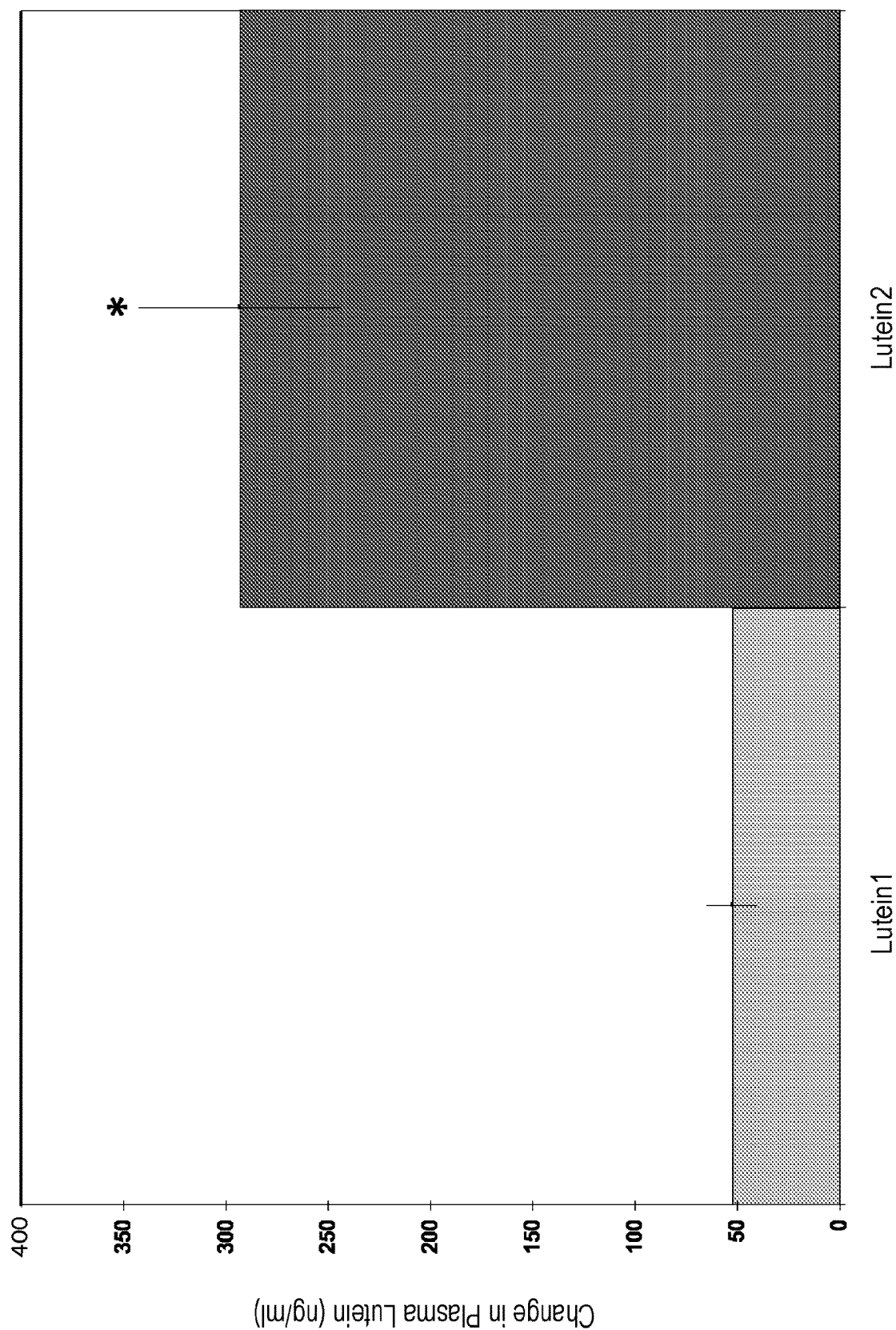
FIG. 6 is a graph showing the change in plasma lutein concentrations after 10 days of supplementation with 10 mg/day of lutein. Lutein 1=lutein ester. Lutein 2=solid-lipid particle complex. *Significantly different from pre value, $p<0.002$, unpaired t-test.
Figure 7:
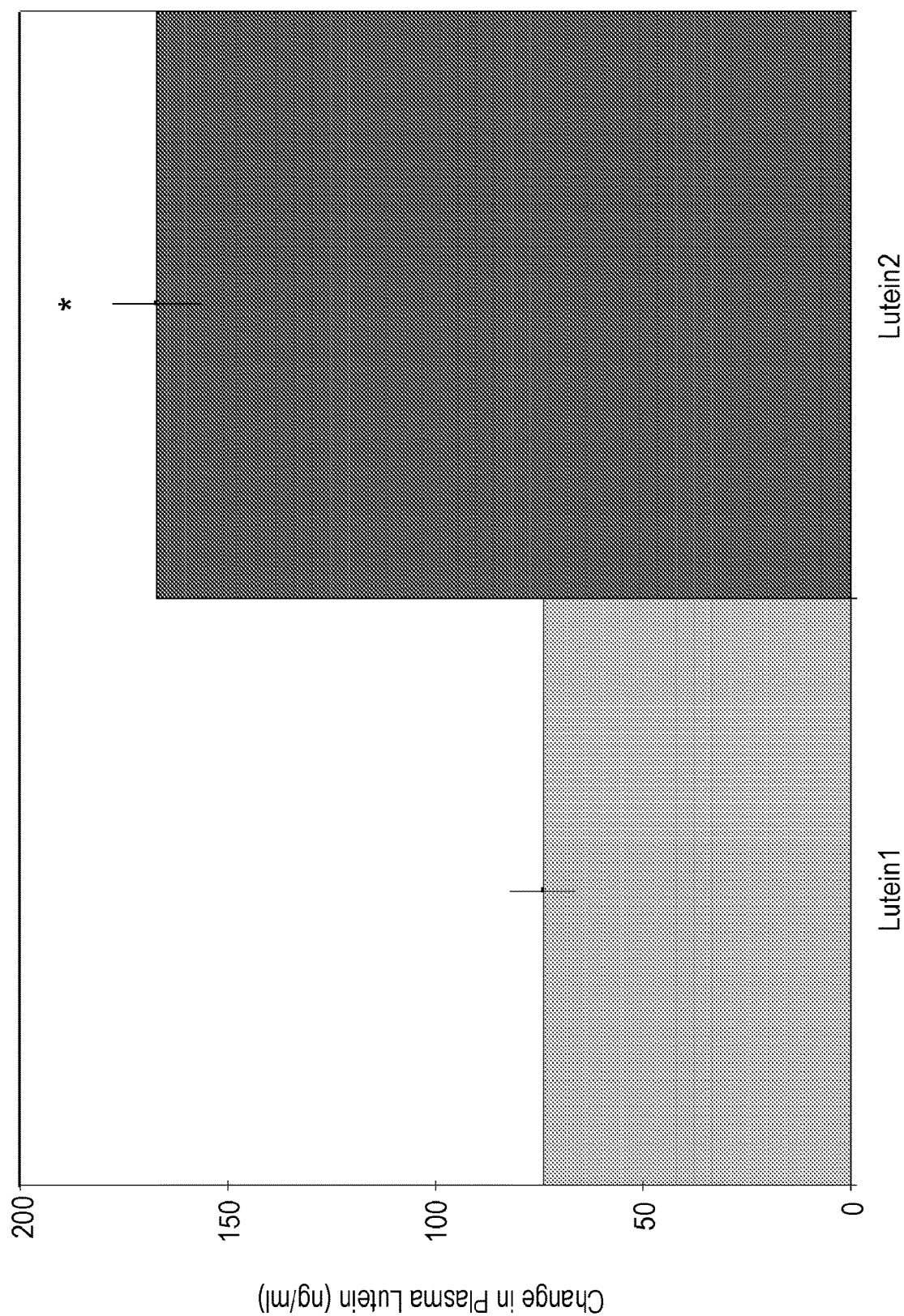
FIG. 7 is a graph showing plasma lutein concentrations 7 days post-supplementation (10 mg/day of lutein for 10 days). Lutein 1=lutein ester. Lutein 2=solid-lipid particle complex lutein. *Significantly different from pre value, $p<0.001$, unpaired t-test.

Changes within each supplement group were analyzed by paired t-test using http://www.fon.hum.uva.nl/Service/Statistics/Student_t_Test.html Group comparisons were done by unpaired t-test using http://www.fon.hum.uva.nl/Service/Statistics/2Sample_Student_t_Test.html Results After 10 days of supplementation, both supplements produced highly significant increases in plasma lutein values (FIG. 5, $p<0.001$ for each treatment, paired t-test). The solid-lipid particle complex lutein gave a much higher mean plasma lutein value than conventional lutein ($p<0.001$, unpaired t-test). The mean percent change versus pre-supplement values was 563% for the solid-lipid particle complex lutein and 88% for the conventional lutein ester. If the data was expressed as the change in lutein concentrations, a much higher mean change was seen with the solid-lipid particle complex (FIG. 6, $p<0.001$, unpaired t-test). For both the conventional and new lutein supplement, mean plasma lutein levels remained above baseline 7 days after supplementation (FIG. 5, pre-values vs FIG. 7, $p<0.001$, paired t-test). However, the solid-lipid particle complex lutein gave a much higher mean plasma lutein value (FIG. 7, $p<0.001$, paired t-test). Thus, by three types of evaluations, plasma lutein concentrations responded to a much greater degree to the solid-lipid particle complex lutein than to a conventional version.

In summary, a 10 day supplementation of solid-lipid particle complex lutein produced far greater plasma levels as compared to lutein ester. Not to be bound by any particular theory, the higher plasma lutein concentrations produced by the solid-lipid particle complex lutein is thought to reflect better absorption from the GI tract.

Example 4: *Bacopa Monnieri* Formulations with Improved Pharmacokinetic Properties

*Bacopa monnieri* (BM) is from the family Scrophulariaceae. It has been used as brain tonic and restoration in debilitating diseases. It is found in Indian subcontinent in wet, damp marshy areas and is used by Ayurveda in India for 3000 years and is classified as a medhyarasayana in Ayurveda, a drug used to improve memory and intellect (medhya). Bacopa is also used in diseases like Alzheimer's and dementia. BM may be used for treatment of numerous mental health disorders.

The problem with commercially available BM formulations is that its recommended dose for the disease is high and duration of therapy is long which might indicate that the permeability of bacosides into the brain is meager. The longer therapy with high doses causes gastric irritation. This disclosure provides a formulation using the delivery system of the present description that improves availability of the BM, increases the amount of BM that traverses the blood brain barrier (BBB) and reduces the duration of therapy.

Material and Methods

The phase A of study comprised of BM Extract (BME) formulation development, and quality control analysis which was conducted at M/s Pharmanza Herbal Pvt. Ltd. Anand, Gujarat, India on our personal request and liaison.

The phase B of the study comprised of preclinical kinetic study of the newly developed formulation, controlled and standard formulations. In the kinetic study 27 albino rats were used in three groups (nine each) for estimation of bacosides in blood at different time intervals. At the end of experiment, the animals were killed and their brains were extracted. The excised brains were homogenized and level of bacosides in the brain tissue was measured. The levels of bacosides were compared in both the blood and brain samples. The pharmacokinetic study was approved by the institutional animal ethics committee of the IFTM, University Moradabad. U.P. India.

Phase A

Development of Standard Formulation

Standard formulation of BM (F1): Whole plant of BM, harvested during the months of March to June (Mathur S, Gupta M M, Ram M, Sharma S, Kumar S. Herb Yield and Bacoside-A Content of Field-Grown *Bacopa monnieri* Accessions. J Herbs Spices Med Plants. 2002; 9(1):11-8), originating from India, was collected and washed thoroughly with water. The BM plant was confirmed and then whole plant of BM was pulverized and its methanolic extract was prepared. Methanol was evaporated to get the dried form, which was then pulverized and analyzed by gas chromatography for impurities related to residual solvents.

Partition Coefficient

Partition coefficient being the important parameter to determine the hydrophylicity and lipophylicity of a compound, determination of partition coefficient value was done by online free software: Molinspiration. It also supports internet chemistry community by offering free on-line services for calculation of important molecular properties (log P, polar surface area, number of hydrogen bond donors and acceptors and others), as well as prediction of bioactivity score for the most important drug targets (G-protein coupled receptor, ligands, kinase inhibitors, ion channel modulators, nuclear receptors) (Calculation of Molecular Properties and Bioactivity Score. 2014. http://www.molinspiration.com/cgi-bin/properties. Accessed 15 Oct. 2014). Experimentally the partition coefficient was determined by shake flask method, using two immiscible liquids, one being n-octanol and the other being water.

Development of New Formulation of BME

The New formulation (F2): Part A: Twenty gram of the extracted powder was mixed with 200 ml of methanol, and then refluxed for 2 hr. Part B: Four gram of Phosphatidylcholinephospolipid (90%) was mixed with 100 ml of water. Then part A and B were mixed, the solution was concentrated by rotator evaporator, and then 50 ml reverse osmosis water was added. The solution was concentrated for removal of methanol traces, then after addition of 90 ml water, solution was homogenized for 45 min at 1400 RPM (micro emulsification of liposomes). Then the solution was spray dried in lab plant 0.5 D-05 at 173° C. and 0.6 kg pressure, to obtain the bacopa powder. The formulation F3 and F4 were prepared by the use of same procedure as applied for formulation F2 with 4 gm Phosphatidylethanolamine and 4 gm Cholesterol respectively. All the formulations (F1, F2, F3 and F4) were analyzed on the basis of physical, chemical, microbiologcal and impurity analysis.

Selection of Formulations

On the basis of release profile of different formulations most suitable lipophylic substance was selected and different concentrations of that selected substance were prepared for further study.

On the basis of above, the most suitable material was found to be phosphatidylcholine and then its four new formulations with different concentrations, P1 (10%), P2 (20%), P3 (30%) and P4 (40%) were prepared by applying same procedure as previously applied for the development of F1-F4. On the basis of release profile of formulations with different concentrations of phosphatidylecholine (P1-P4), the most suitable concentration was selected for animal studies.

Phase B

Dose Calculation

Dose of the BM formulation were calculated from the formula specified (Shaw S R, Nihal M, Ahmad N. Dose translation from animal to human studies revisited. FASEB J. 2008 March; 22(3):659-61).

HED: Human effective dose mg/kg,

Km: kilogram per meter square $$HED = \text{Animal dose } \frac{mg}{kg} \times \frac{\text{animal Km}}{\text{human Km}}$$

Animal Experiments

Animal experiments were performed on albino rats of either sex. Three groups of the albino rats were formed (control, standard and test). Each group was further subdivided into three subgroups with each subgroup having three animals. Doses were administered orally in suspension form as per the rat's body weight.

Estimation of Bacosides in rat Blood; blood was withdrawn at specific time intervals (0, 12, 22.5, 45, 90, 180, 360, 720, and 1440 min) and concentrations of bacosides in serum were analyzed by liquid chromatography-mass spectrometry (LCMS).

Estimation of Bacosides in rat Brain; after 24 hours of administration of the formulation, animals were killed and the brains were extracted, homogenized and then centrifuged at 4000 rpm for 15 min. The supernatant were collected and analyzed by LCMS.

Liquid Chromatography-Mass Spectrometry

Liquid chromatography conditions:

Instrument: Waters—Q-Tofmicromass, Column: C18× terra, Particle size: 5 μm 2.1×100 mm, Flow rate: 0.15 ml/min, Acetonitrial: 0.1% TFA in water 35: 65, λ=205 nm Mass Spectrometry Conditions:

Capillary voltage: 3000, Sample cone: 28-30 volt, Extraction cone: 1.0, Sours temp: 100 C, Desolation temp: 303

Statistical Analysis

Results were analyzed by applying software "primer of biostatistics" product version 4. P value less than 0.05 was considered as significant and means were compared with using repeated measure ANOVA and multiple comparison was done by using post-hoc Turkey test.

Results

Determination of Partition Coefficient

Determination of partition coefficient and other factors was performed with the help of online software, molinspiration.com. In BME, the bacosides are a group of chemical compounds which are responsible for the memory enhancing property of BM. But the different chemical components in BME, A3, II, X and C have different log p values (0.66, 0.5, 1.12 and 1.47) and concentrations (18.42, 36.72, 13.28 and 14.02 percent) respectively. The partition coefficient of BME was found 0.8363, and the values of Ames test of A3, II, X and C were 89, 89, 81, and 85 respectively.

Shake Flask Method for the Determination of Partition Coefficient;

This method being easy and reliable was used to determine the log P value of the compound where we use the two immiscible liquids, one being n-octanol and the other being water. N-octanol is considered as suitable barrier matching body barriers so we used the n-octanol and water to define the lipophylic and hydrophilic barriers in the body cells.

Assay by Ultraviolet Spectroscopy $$\% \text{ Bacoside} = \frac{\text{Absorbanceat (278 nm)} \times 50.9577 + 1.2978 \times 100}{\text{SampleConcentration}}$$

$$\text{Partitioncofecient} = \frac{\text{Concentration-inorganic-phase}}{\text{Concentration-onaqueos-phase}}$$

$$\text{Partitioncofecient} = 45.48/54.52$$

$$\text{Partitioncofecient} = 0.8342$$

The value of partition coefficient indicated the hydrophilic nature of BME.

Impurities (Residual Solvents)

By using gas chromatography, all the residual solvents like Isopropanol, Ethyl acetate, Ethanol, Acetone, Chloroform, Cyclohexane, Tolune, Methanol, n-Hexane, Benzene and 1, 2-dichloroethane were present as per the permitted USP limit.

Analysis of the BM Formulations

Pre Formulation Studies;

The identification tests for all formulations were positive by TLC method. The plant part used being whole plant, appearance being fine powder, colour greenish brown to brown, odor and taste were characteristic organoleptic for all formulations. Particle size of all preparations through mesh no. 30 were as per the limit specified in USP, bulk density and tap density of all formulations was under the limit specified in the USP.

Chemical Analysis;

The assay of bacosides in all formulations were measured by UV and HPLC. It was found that the concentration of bacosides varied in different formulations and was highest in control formulation with 45.23% by UV and 15.17% by HPLC and less in others. The concentration variation was due to the fact that other forms also have added excipients in the formulations. Other parameters like loss on drying, herb extract ratio, moisture content, pH, acid insoluble ash, excipients and solvents were under the limits specified in USP.

Microbiology;

The microbiological study of all the formulations showed that all parameters (Total plate count, Yeast and Mold, Coilform, *Escherchia coli*, *Salmonella*, *S. aurens*, Enterobacteriaceae) were under the limits specified in USP. Thus it indicates that all formulations used were microbiologically safe for use.

Impurities (Heavy Metals);

Literature shows that the impurities of heavy metals like total heavy metals, lead, mercury, cadmium, and arsenic are present in herbal preparations [12]. However, analysis of our all formulations of BME showed that the data was under the limit specified in USP.

Estimation of Bacosides in Rat Brain

Figure 10A:
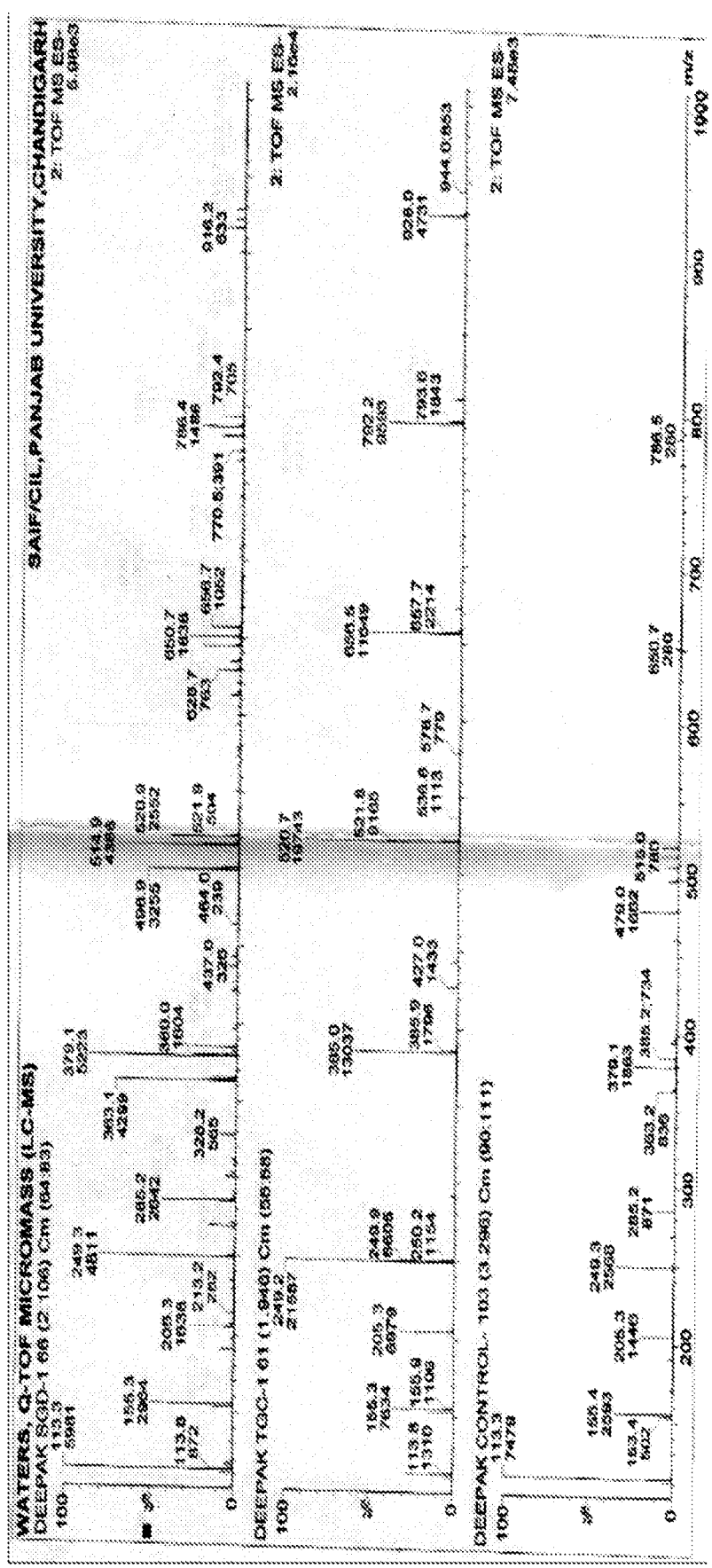
FIG. 10A-B show the intensity and molecular weight of bacoside A3 and their metabolites in the blood plasma with the control (distilled water), standard (F1) and test formulation (P2).
Figure 10B:
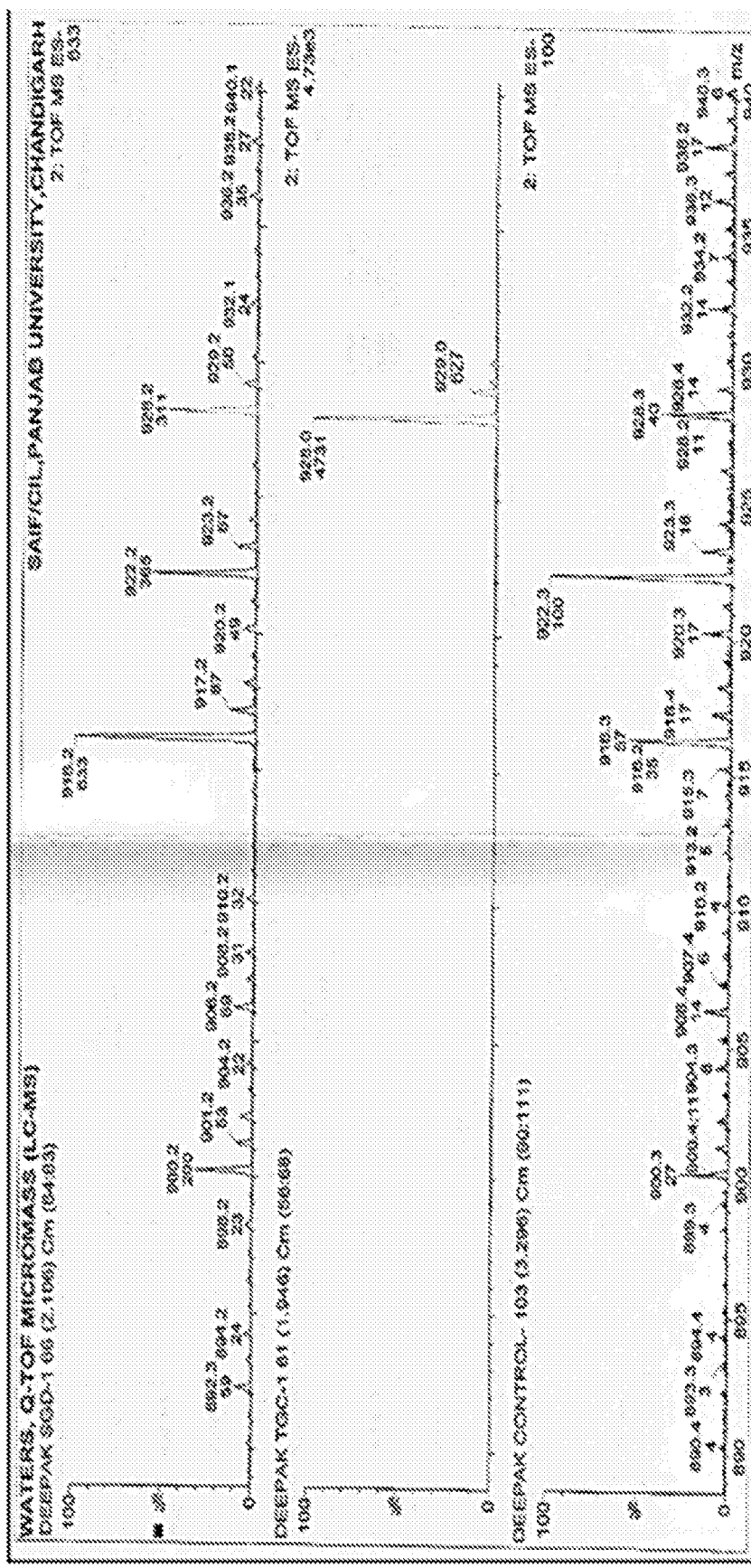

The control group (distilled water); in FIGS. 10 (a) and (b), the peaks with molecular weight and intensity 786.5 (280), 650.7(280), 516(780) were found in the control group. Many other peaks with different molecular weights were also revealed at very low intensity 100e.

Standard group (F1); on the analysis of standard group, it was found the bacosides A3 with the molecular weight (MW) 929.2 and intensity 50 and by the removal of one electron, MW 928.2 with the intensity of 311 was found. Other metabolites with different intensities like 923.2(67), 922.2(365), 920.2(49), 917.2 (87), 916.2(633), 792.4 (705), 656(1052), 628.7(763), 521.9(504) and 520.9 (2552) were also seen.

Test group (P2); analysis of the test group showed that the bacoside A3 had MW 929.2 with intensity 627 and with the removal of two electrons different metabolites 929.0 (627), 928 (4731), 793 (1843), 792.2 (9593), 657.7 (2214), 656.5 (11649), 578.7 (779), 536.8 (1113), 521.8 (9165), 520.7 (19743) were found.

Estimation of Bacosides in Rat Brain

Control Sample;

In the analysis of brain samples in control group of rats it was found that the peaks were at 922.5 (14), 922.4 (45), 922.3 (30), 917.4 (13), 916.4 (51), 916.3 (10), 900.5 (15), 900.4(24), 900.3 (10).

Standard sample (F1); on the analysis of brain sample of rats with standard formulation, it was found that the concentration of bacoside and their metabolites were 928.4 (22), 922.4 (98), 922.3 (41), 916.4 (56), 916.3 (129), 916.2 (13), 910.3 (10), 900.4 (19), 900.3 (13), 894.4 (8), 884.4 (9), 877.4 (6), 871.4 (5), 515 (961).

Test sample; on the analysis of brain samples of rats with test formulation, it was found that the concentration of bacoside and their metabolites were 928.4 (44), 923.3 (11), 919.1 (21), 918.1 (66), 916.4 (17), 910.4 (23), 910.3 9 (12), 895.5 (15), 894.4 (24), 886.4 (7), 882.4 (8), 878.4 (15), 877.4 (26), 877.3 (71), 875.3 (11), 852.3 (23), 644.8 (588), 537 (754), 508 (2081).

Discussion

After the development of standard formulation of BME, it was analyzed for the impurities related to residual solvents and the inventors found that impurities were either not detected or were under the USP limits. This indicates that this formulation is safe for the oral administration and there were no impurities which are harmful to the recipients.

The result of Ames test of Bacopaglycoside C, II, X, A3 by online software molinspiration (Calculation of Molecular Properties and Bioactivity Score. 2014. http://www.molinspiration.com/cgi-bin/properties. Accessed 15 Oct. 2014), showed the compounds do not have the mutagenic potential and thus are not harmful for the recipients (The Ames test for mammalian environmental mutagenicity. 2014. http://www.mun.ca/biology/scarr/4241_Ames_Test.html. Accessed 21 Nov. 2014).

Determination of Partition Coefficient

The partition coefficient was estimated by software molinspiration.com and by shake flask method (Lin B, Pease J H. A novel method for high throughput lipophilicity determination by microscale shake flask and liquid chromatography tandem mass spectrometry. Comb Chem High T Scr Journal. 2013 December; 16(10):817-25). The values of log P were found to be 0.836 and 0.834 respectively. These indicate that the nature of BME is hydrophilic and required nearly 20% rise in partition coefficient/lipophylicity to get better efficacy to crosses BBB (blood brain barrier) (KD Tripathi. Essentials of medical pharmacology. 6th edition. Jaypee Brothers Medical Publishers Pvt. Ltd. 20, 2010).

After evaluation of the above parameters, it was concluded that more lipophylic moiety is needed for better capability to cross BBB, and also the value of log P nearer to one provides better pharmacokinetic properties. Hence the inventors formulated four new formulations with different lipophylic agents viz. Control form, Phosphatidylcholine, Phosphatidylethanolamine and Cholesterol.

Analysis of the BM Formulations

On the analysis of formulations, the parameters related to Preformulation studies, Chemical Analysis, Microbiology and Impurities relating to heavy metals were found to fulfill the criteria of USP. The only difference in the assay of bacopa in formulations was due to the presence of excipients.

Figure 8:
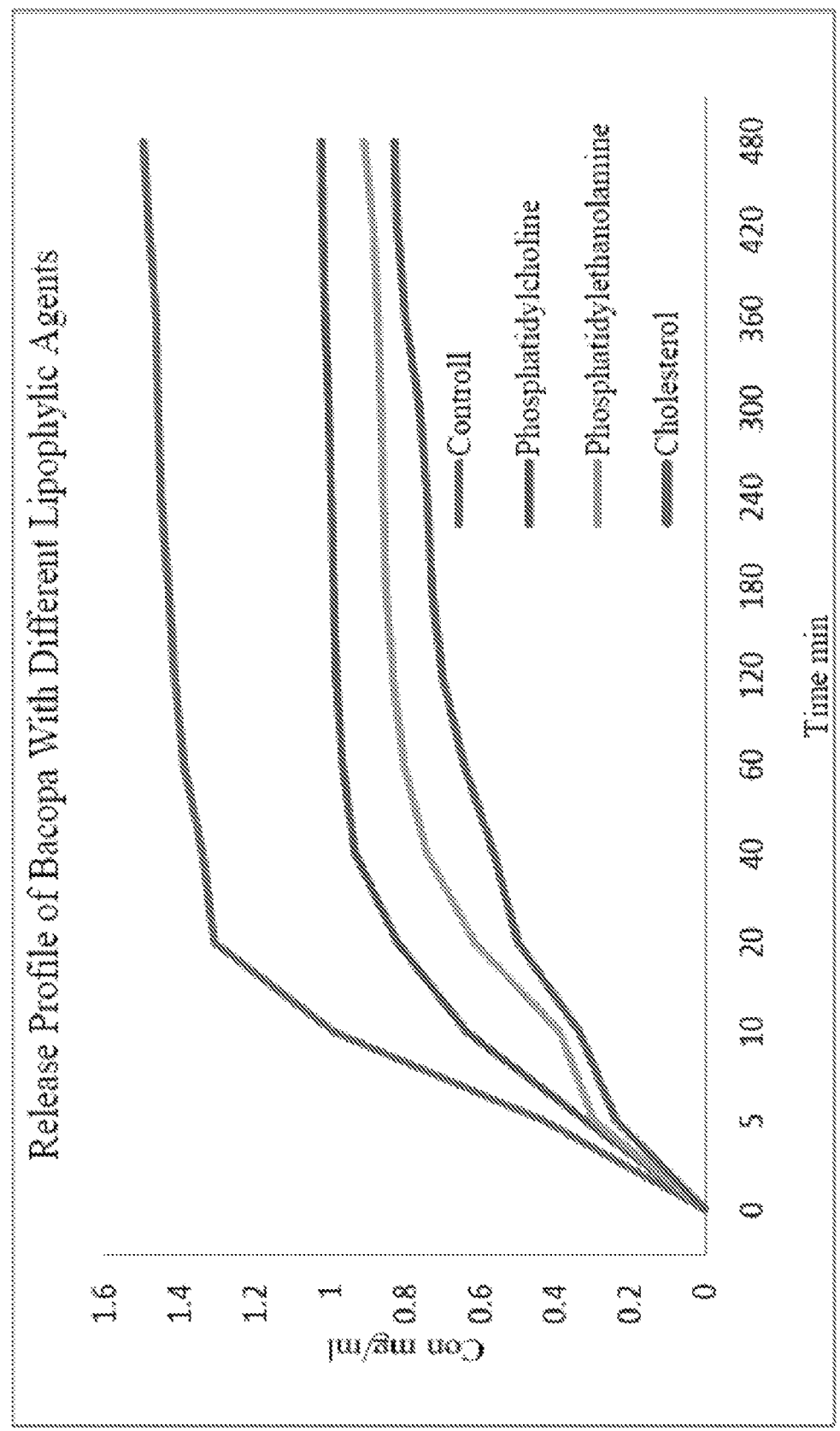
FIG. 8 shows the release profile of bacopa with different lipophylic agents. The best release profile was of control formulation, followed by phosphatidylcholine, phosphatidylethanolamine and cholesterol.

Comparative Study of Release Profile of Formulations Based on Different Lipophylic Agents;

The best release profile was of control formulation which decreased with phosphatidylcholine, phosphatidylethanolamine and cholesterol respectively (FIG. 8). This was indicative of the maximum release profile seen with the control formulation, second with phosphatidylcholine and third with phosphatidylethanolamine and last with the cholesterol. This indicates that as the lipophylicity of the formulation increased, the release profile decreased. According to this, control formulation which was without any lipophylic agents had the best release profile.

As per the previous reports (Goswami S, Saoji A, Kumar N, Thawani V, Tiwari M, Thawani M. Effect of *Bacopa monnieri* on Cognitive functions in Alzheimer's disease patients. IJCRIMPH. 2011; 3(4):285-93), the control formulation did not have better permeability to cross BBB hence requires higher dose for longer duration to increase its effect in brain. This increased dose and duration leads to GI irritation and hence poor patient compliance. The new formulation of BME with lipophylic agents increased the ability of BM to cross the BBB.

Based on the above results, formulation phosphatidylcholine (F2) was selected for further study on the basis of its favorable hydrophilic and lipophylic profile which also has better permeability across BBB. F2 also had an adequate elimination rate.

When the release profile was analyzed statistically; all values were found statistically significant except when compared in between phosphatidylethanolamine vs cholesterol. It indicated that there was significant difference in release pattern among different formulations (FIG. 8).

Suitable Concentration of Phosphatidylcholine for Our Formulation of BME;

After the selection of the suitable lipophylic agent, the inventors determined the most suitable concentration of Phosphatidylcholine for the preparation of new formulation of BME. Four new formulations with different concentrations of Phosphatidylcholine were prepared. P1, P2, P3, and P4.

On the basis of analysis of these formulations, the inventors found that all the parameters related to physical, chemical, microbiological and impurities were under the limit specified by USP/conformed to it or were absent. This indicates that all the formulations were acceptable for oral use.

Figure 9:
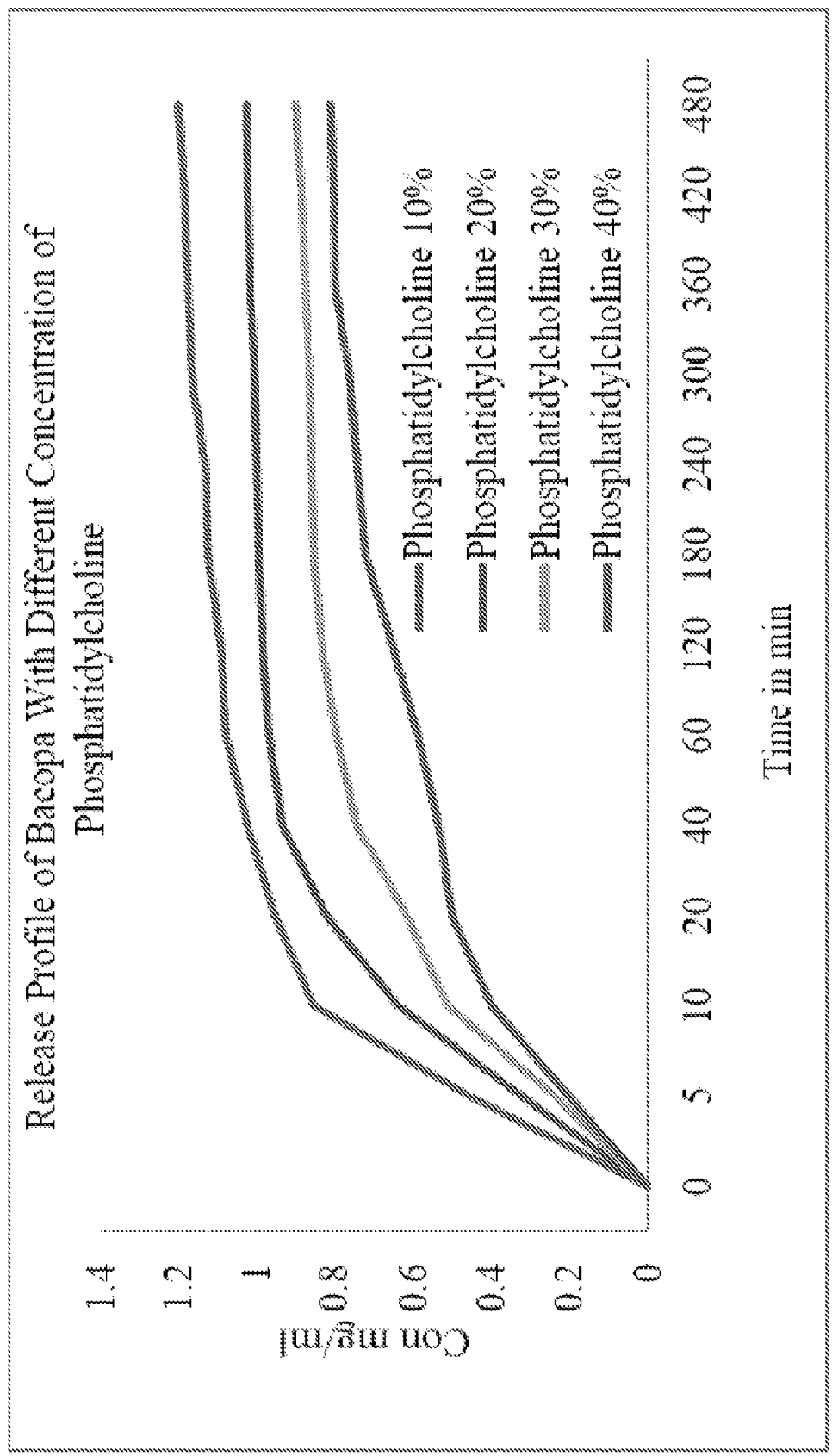
FIG. 9 shows a graph of the release rates. On the basis of dissolution profile of different concentration of phosphatidylcholine formulations, phosphatidylcholine with 10% concentration had highest release rate, whereas phosphatidylcholine with 40% concentration had lowest release rate.

On the analysis of the release profile of BM with different concentrations of Phosphatidylcholine, maximum release was seen with 10% Phosphatidylcholine while the lowest was seen with 40% Phosphatidylcholine (FIG. 9), which indicated that the best dissolution profile was of formulation P1. According to the partition coefficient value, formulations required nearly 20% rise in log P value. Thus, formulation P2 (based on 20% Phosphatidylcholine) was used for further animal experiments. On statistical analysis of release profile of different concentration of phosphatidylcholine, P value indicated that all the results were statistically significant.

Comparison of Standard and Test Formulation

We found that all the physical, microbiological and impurities related parameters were nearly same as per the limits specified in national formulary USP/conformed or absent. The only difference in chemical analysis, the concentration of bacosides being 45.23, 35.45% by UV and 15.17, 10.25% by HPLC, respectively, due to increased amount of excipients in the BM sample. The water soluble extractive was decreased and alcohol soluble extractive increased in the formulation P2. The pH of formulation P2 was slightly higher and other parameters were nearly same or under the limits specified in Indian pharmacopeia and USP.

After the comparative analysis of F1 and P2, it was concluded that the formulation of BME based on phosphatidylcholine 20% had less concentration of bacosides then standard formulation of BME and slightly higher pH, which may be due to the addition of phosphatidylcholine.

Animal Experiments

Comparison of Blood and Brain Samples by LC-MS

As per the literature, the compound mainly responsible for memory enhancing property is bacoside A3 and II. The molecular structure and molecular weight of both are the same (molecular weight i.e. 929.10) but the difference was only in the optical rotation of the compound bacoside A3 (Levorotatory) and bacoside II (Dextrorotatory).

Mass Spectrophotometric Comparison of Control, Standard and Test Group in Blood.

According to the FIGS. 10 (a) and (b) the control group showed many peaks with different molecular weights. On the comparison of standard and test formulations, the inventors found that the amount of Bacoside A3 and their metabolites were found in greater amounts in test then the standard group. It directly indicated the amount of bacosides was more with the test formulation in rat plasma.

Plasma Concentration v/s Time Profile

Figure 11:
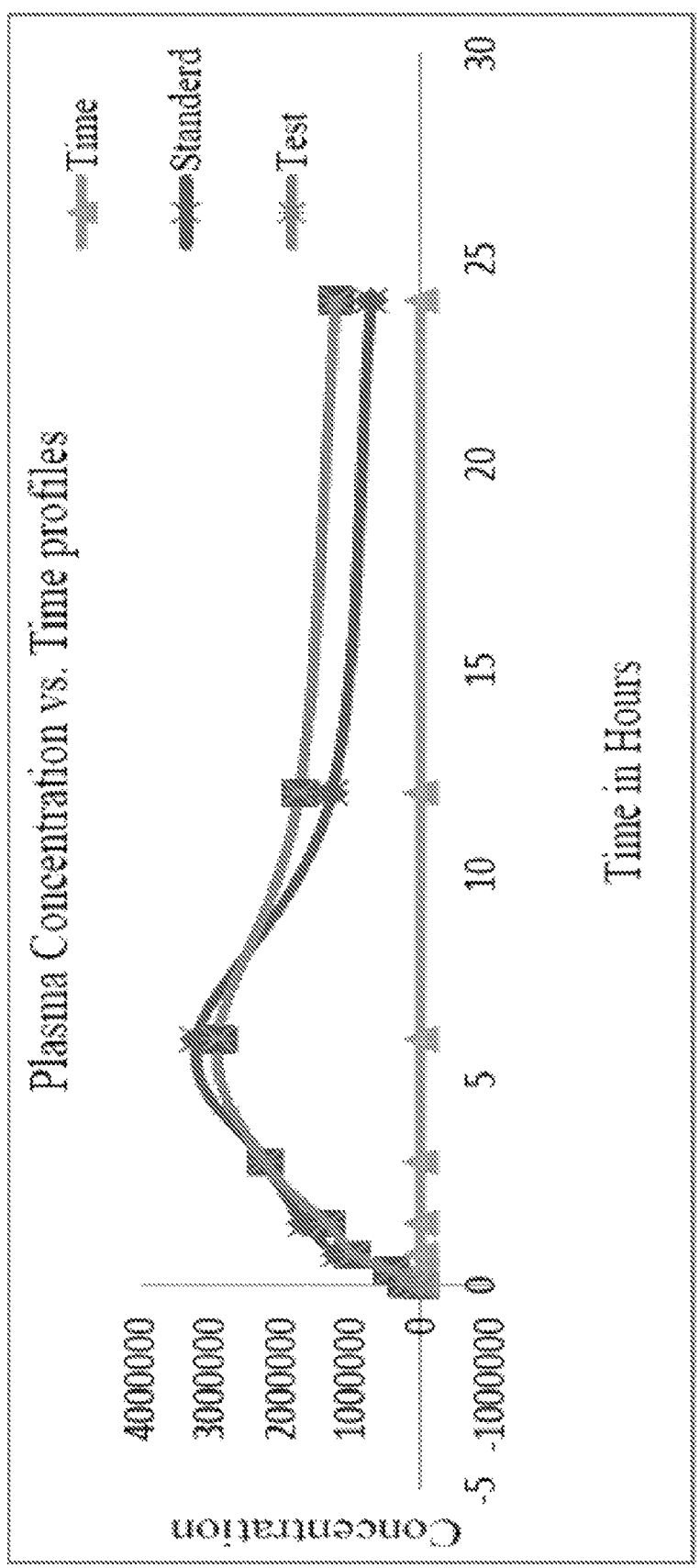
FIG. 11 demonstrates the results of plasma concentration over time. Test formulation (P2) showed better AUC value, whereas $C_{max}$ was higher of standard formulation (F1). $T_{max}$ of both formulations was nearly same.
Figure 12:
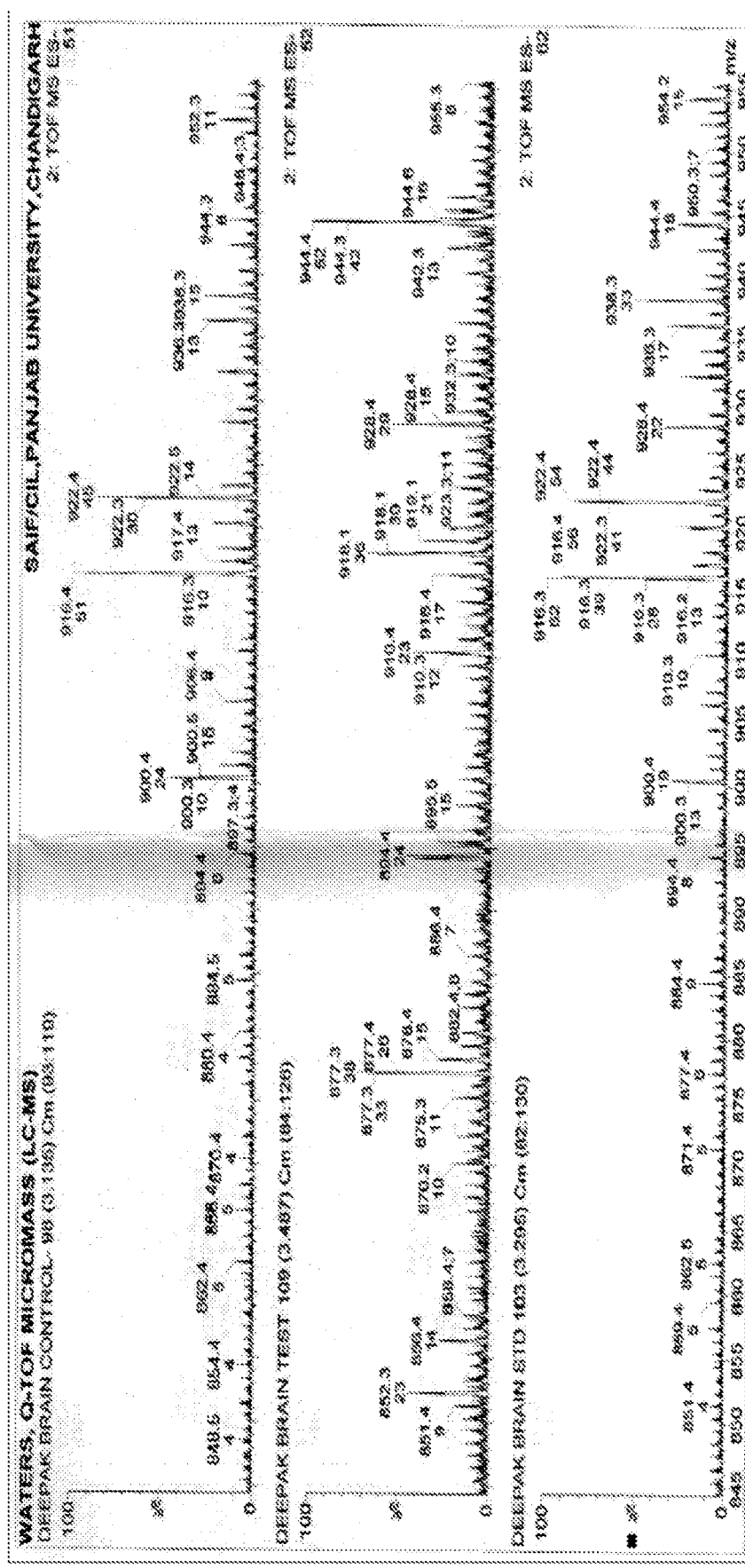
FIG. 12 shows the comparison of different administered formulation of bacoside A3 and their metabolites by mass spectrometry. It was observed that bacoside A3 and its metabolites were in high concentration in rat brain with the test formulation (P2) than standard and control formulations.

As per FIG. 11, the plasma concentration vs time was plotted in the rat model. The standard formulation showed the highest concentration ($C_{max}$) after six hours of dose administration and the elimination rate was also high. The test formulation also showed the $C_{max}$ at six hours, but concentration was lesser then standard formulation and the elimination rate was also slower than standard. The area under the curve (AUC) of test formulation was also more than standard formulation which indicated that the test drug had better pharmacokinetic profile.

Mass Spectrophotometric Comparison of Control, Standard and Test Group on Brain Samples Analysis of the plasma and brain samples of rats demonstrated high concentration of bacosides and their metabolites in test formulation compared to the standard formulation, which indicated better penetration of bacosides and their metabolites into the brain by the new test formulation using the delivery system of the present invention.

The mass spectroscopic graph of the brain shows high intensity of bacoside A3 of molecular weight 929.10 and their metabolites which indicated the concentration of bacosides and their metabolites to be higher in the brain with the new formulation, indicating higher permeability of bacosides and their metabolites into the rat brain.

The new formulation had more permeability to cross the BBB and its duration of action was longer.

The new lipophylic formulation of *Bacopa Monnieri* has better penetration into the brain due to the increased lipid solubility and has better pharmacokinetic profile then previously marketed formulations. Due to high penetration of bacosides and their metabolites in the brain, the dose, frequency and duration of therapy will be decreased, and the side effects will also decrease. Hence the patient compliance and quality of life of the patient suffering from Alzheimer's and dementia will improve with our new formulation of Bacopa.

Example 5: Randomized, Double-Blind, Double-Dummy, Placebo-Controlled Trial of Solid Lipid *Boswellia serrata* Particles (SLBSP) Versus Standardized *Boswellia Serrata* Gum Resin Extract (BSE) For Symptomatic Treatment of Osteoarthritis of Knee Ethnopharmacological Relevance:

Osteoarthritis of the knee (OA knee) is a chronic, progressive, skeletal, degenerative disorder often associated with restricted mobility and poor quality of life. NSAIDs are often employed in OA for symptomatic treatment of pain. Boswellic acids (BA) have anti-inflammatory properties and are traditionally used for the treatment of OA knee. However, pharmacokinetic studies have shown low bioavailability of BA including 11-keto-β-boswellic acid (KBA) and acetyl-11-keto-β-boswellic acid (AKBA). Phospholipid complexation enhances the bioavailability of BA, which led to the development of Solid Lipid *Boswellia serrata* Particles (SLBSP).

Methods:

It was a prospective, randomized, double-blind, double-dummy, placebo-controlled, single-center clinical trial in patients with symptomatic OA knee. Subjects were randomized to receive either SLBSP capsules or BSE tablets using a computer generated random sequence. Allocation concealment was achieved with the help of sealed envelopes to eliminate selection bias. Matching placebos resembling SLBCP capsules and BSE tablets were formulated and each patient received an active drug and a placebo (i.e., SLBSP capsule+BSE Placebo or BSE tablet+SLBSP placebo). Each tablet of BSE contained 333 mg of standardized BSE gum comprising 40% Boswellic acids (BA) whereas each SLBSP capsule contained 333 mg of the formula equivalent to 100 mg of 40% Boswellic acids Treatment was continued for two months. Patients were allowed to take rescue analgesics (Acelofenac 100 mg) as and when required. Improvement in pain and function was assessed with the help of Western Ontario and McMaster Universities OA index (WOMAC), Visual Analog Scale (VAS) and need for rescue analgesics at one month and two months. Cross Linked telopeptide of Type II Collagen (CTX-II) was measured in urine at baseline and end of treatment. Serum levels of inflammatory cytokines including IL-2, IL-4, IL-6, TNF-α, IFN-γ was measured at baseline and at the end of treatment. The outcomes were compared between the two groups using ANOVA.

Results:

Twenty patients were enrolled in each arm. Both treatments resulted in marked improvement in pain and function scores compared to baseline. WOMAC score improved by 18.2% and 15.4% at 1 month and two months respectively in the SLBSP arm ($p<0.05$) whereas the corresponding figures for BSE was 18.8% and 23.1% ($p<0.05$) respectively. Similar change was observed in VAS score i.e., 19% and 26% improvement respectively ($p<0.05$) during the same period for BSBSP and 18.2% and 20.4% improvement respectively ($p<0.05$) in the BSE arm. The difference in VAS and WOMAC scores between the two arms was not statistically significant. However, the most significant effect was observed in the need for rescue analgesics which reduced markedly by 67% during the first month and 76% in the second month in SLBSP arm whereas it was 65% and 34% respectively in the BSE arm compared to baseline ($p<0.01$). SLBSP resulted in markedly lower dependence on rescue analgesics compared to BSE at the end of 2 months ($p<0.05$). SLBSP also caused marked lowering of IL-2 and IL-4 levels as compared to baseline whereas a several fold increase was noted in the levels of these proinflammatory cytokines in the BSE arm (p<0.05). No significant difference was observed in other cytokines or urine CTX-II levels between the two arms. No adverse effects were observed due to either treatment. Compliance to treatment was greater than 80% in all patients in both arms.

Conclusion:

Both SLBSP and BSE caused marked improvement in pain and function scores in patients of OA knee but SLBSP was superior to BSE in reducing the need for rescue analgesics in addition to modulating inflammatory cytokines.

Example 6: Comparison of Two Types of Coenzyme Q Supplements for Effects on Plasma Coenzyme Q and Vitamin C Concentrations Design A. Study Population. Subjects will be non-smoking, healthy people, 50-75 years old. This age group was should not have high CoQ stores since organ CoQ contents can fall as people age. Subjects will not have been consuming vitamin C containing supplements at over 100 mg/day (a common amount in multivitamins). If prior to study participation, a subject is using a multivitamin supplement with 100 mg of vitamin C, then that product will be discontinued for at least 4 days before beginning participation.

B. Procedures. For 2 weeks, subjects will consume one of the flowing daily with a fat containing meal:

Control: Placebo capsule (gelatin)

CoQ (100 mg/day, standard)

CoQ (100 mg/day, new using granules of the present technology)

Each treatment group will have 15 subjects drawn from both genders (about the same split per group). During the 14 day intervention, subjects will be asked to not eat certain high vitamin foods (citrus fruits and their juice, kiwi, strawberries, drinks with 50 mg or more of added vitamin C/serving, green and related peppers, kale and broccoli).

C. Analysis. The main project measurements, plasma coenzyme Q and ascorbic acid, will be analyzed by HPLC in a contracted laboratory. Also, plasma malondialdehyde will be analyzed using a kit from Calbiochem at their facilities.

While in the foregoing specification this invention has been described in relation to certain embodiments thereof, and many details have been put forth for the purpose of illustration, it will be apparent to those skilled in the art that the invention is susceptible to additional embodiments and that certain of the details described herein can be varied considerably without departing from the basic principles of the invention.

All references cited herein are incorporated by reference in their entirety. The present invention may be embodied in other specific forms without departing from the spirit or essential attributes thereof and, accordingly, reference should be made to the appended claims, rather than to the foregoing specification, as indicating the scope of the invention.

We claim:

1. A delivery system having enhanced oral bioavailability comprising:
 a carrier granule with a particle size from about 150 to about 840 microns,
  wherein the carrier granule comprises an agglomeration of solid lipid particles for oral dosing,
   wherein the solid lipid particles comprise one or more long chain lipid selected from the group consisting of soy lecithin, phosphatidyl choline, stearic acid and ascorbyl palmitate,
   wherein the ratio of stearic acid:phosphatidyl choline is in a range of about 1.25:1 to about 3.5:1,
   wherein the solid lipid particles within the granule have a particle size from about 5 to about 20 microns and wherein the solid lipid particles are encased within the carrier granule, and
 one or more biologically active compounds, wherein the biologically active compound is curcumin or lutein.

2. The delivery system of claim 1, wherein the solid lipid particles comprise one or more long-chain lipid.

3. The delivery system of claim 1, wherein the solid lipid particles further comprises dextrin, silicone dioxide or both.

4. The delivery system of claim 1, wherein the biologically active compound comprises a lipophilic moiety and a hydroxyl group.

5. The delivery system of claim 1, wherein the biologically active compound comprises curcumin.

6. The delivery system of claim 1, wherein the biologically active compound comprises lutein.

7. The delivery system of claim 1, wherein the carrier granules comprise a core consisting of the active ingredient, phosphatidylcholine and ascorbyl palmitate and a coating of stearic acid.

8. The delivery system of claim 1, wherein the active ingredient is embedded in or adhered to the surface of carrier granule.

9. The delivery system of claim 1, wherein the solid lipid particles are enchased within the granule.

10. The delivery system of claim 1, wherein the carrier granule is formed from fractured solid lipid microparticles.

11. The delivery system of claim 1, wherein the carrier granule comprises solid lipid microparticles embedded in or adhered to the carrier granule.

12. The delivery system of claim 1, wherein the carrier granule increases the delivery of the active agent to the lymphatic system.

13. The delivery system of claim 1, wherein the carrier granule increases the solubility of the active ingredient in water.

14. The delivery system of claim 1, wherein the granules protect the active ingredient from hydrolysis in the gut.

15. The delivery system of claim 1, wherein the delivery system is absorbed by the lymphatic system.

16. The delivery system of claim 1, wherein the granule avoids first pass metabolism in the liver and increases bioavailability of the active ingredient.

17. The delivery system of claim 1, wherein the delivery system increases solubility in water of the active ingredient.

18. A delivery system of claim 1 comprising: about 15-40% of at least one active compound; about 7-25% Soya lecithin; about 7-30% Maltodextrin; about 1-3% Ascorbyl palmitate; and about 0.3-2% Silicone dioxide.

19. The delivery system of claim 18, wherein the soya lecithin is phosphatidyl choline.

20. A delivery system of claim 1 comprising: about 10-30% of at least one active compound; about 10-20% of phosphatidylcholine; about 25-35% stearic acid; about 25-40% dextrin; and about 1-4% ascorbyl pa lmitate; and a bout 0.1-3% silicon dioxide.

21. A method of treating a age-related disease comprising: administering a therapeutically effective amount of the delivery system of claim 1, wherein the delivery system comprises an active ingredient able to treat the age-related disease.

22. A method of making carrier granules of claim 1 for use in a delivery system having enhanced oral bioavailability comprising: a) complexing an active ingredient with purified phosphatidylcholine (80-90% phosphspatidylcholine) and ascorbyl palmitate; b) homogenizing the complex from step (a); c) filtering the homogenized complex; d) spray drying the homogenized complex; e) mixing the dried homogenized complex with melted stearic acid; and f) cooling and milling the material from step (e) to a powder of carrier granules.

* * * * *